United States Patent
Browder et al.

(10) Patent No.: US 12,350,074 B2
(45) Date of Patent: Jul. 8, 2025

(54) STROKE PREDICTION MULTI-ARCHITECTURE STACKED ENSEMBLE SUPERMODEL

(71) Applicant: ASTERION AI INC., Dallas, TX (US)

(72) Inventors: Krag Browder, Colleyville, TX (US); Ezekiel Fink, Dallas, TX (US)

(73) Assignee: ASTERION AI INC., Dallas, TX (US)

( * ) Notice: Subject to any disclaimer, the term of this patent is extended or adjusted under 35 U.S.C. 154(b) by 0 days.

(21) Appl. No.: 18/726,756

(22) PCT Filed: Jan. 4, 2023

(86) PCT No.: PCT/US2023/060120
§ 371 (c)(1),
(2) Date: Jul. 3, 2024

(87) PCT Pub. No.: WO2023/133427
PCT Pub. Date: Jul. 13, 2023

(65) Prior Publication Data
US 2024/0415469 A1 Dec. 19, 2024

Related U.S. Application Data

(60) Provisional application No. 63/266,449, filed on Jan. 5, 2022, provisional application No. 63/266,448, filed on Jan. 5, 2022.

(51) Int. Cl.
*A61B 5/00* (2006.01)
*A61B 5/384* (2021.01)
(Continued)

(52) U.S. Cl.
CPC ............ *A61B 5/7282* (2013.01); *A61B 5/384* (2021.01); *A61B 5/7267* (2013.01); *G06N 20/00* (2019.01); *G16H 50/20* (2018.01)

(58) Field of Classification Search
None
See application file for complete search history.

(56) References Cited

U.S. PATENT DOCUMENTS

| 11,344,248 B1 | 5/2022 | Al-Saggaf et al. | |
| 2011/0312517 A1* | 12/2011 | Giuliani | G01N 33/74 435/7.92 |

(Continued)

FOREIGN PATENT DOCUMENTS

| AU | 2021102581 A4 | 7/2021 |
| WO | 2023133427 A1 | 7/2023 |

OTHER PUBLICATIONS

Albaqami, et al, Automation detection of abnormal EEG signals using wavelet feature extraction and gradient boosting decision tree, Cornell University Library, Dec. 18, 2020, 11 pages.

(Continued)

*Primary Examiner* — Daniel T Pellett
(74) *Attorney, Agent, or Firm* — Definitive Patents; Timothy D. Snowden

(57) ABSTRACT

Apparatus and associated methods relate to emergency stroke detection and classification. In an illustrative example, a stroke detection device may include an ensemble stroke classification model (ESCM). The ESCM may, for example, include class-specific model sets applicable for at least four classes of features, and a general model set applicable for all classes of features. Each model set, for example, may be stacked with multiple class-specific models for each of a corresponding group of architectures. The stroke detection device may, for example, extract predetermined features from a rolling window of a first predetermined duration of EEG data. The predetermined features are extracted and combined into a 1-D input vector. By applying the input vector, the stroke detection device may generate a binary stroke prediction result. Various embodiments may (Continued)

advantageously accurately predict whether a patient is experiencing a stroke within a finite time to assist an emergency service personnel.

20 Claims, 10 Drawing Sheets

(51) Int. Cl.
*G06N 20/00* (2019.01)
*G16H 50/20* (2018.01)

(56) References Cited

U.S. PATENT DOCUMENTS

| | | |
|---|---|---|
| 2016/0042292 A1 | 2/2016 | Caplan et al. |
| 2018/0353084 A1 | 12/2018 | Wainright et al. |
| 2021/0030299 A1 | 2/2021 | Naber et al. |
| 2021/0251497 A1 | 8/2021 | Schulhauser et al. |
| 2021/0251578 A1 | 8/2021 | Schulhauser et al. |
| 2021/0321880 A1 | 10/2021 | Bobo et al. |
| 2022/0061743 A1* | 3/2022 | Christensen ............. A61B 5/31 |
| 2022/0183633 A1 | 6/2022 | Kinzie et al. |
| 2022/0199245 A1 | 6/2022 | Wipperman et al. |

OTHER PUBLICATIONS

Arce-Santana, et al, A-Phase classification using convolutional neural networks, Cornell University, Jul. 22, 2019, 19 pages.

Cantillo-Negrete, et al, Time-Frequency Analysis of EEG Signals from Healthy Subjects Allocated by Gender for a Subject-Independent BCI-Based on Motor Imagery, 6th Annual International IEEE EMBS Conference, Nov. 8, 2013, 4 pages.

Chapter II Demand filed in related International Application No. PCT/US2023/060120, dated Nov. 2, 2023, 17 pages.

Dewi, et al, Stroke severity classification based on EEG signals using 1D convolutional neural network, Journal of Physics: Conference Series, 2020, 7 pages.

Guler, et al, Expert systems for time-varying biomedical signals using eigenvector methods, Science Direct, Nov. 30, 2006, 14 pages.

Gupta, P, Cross-Validation in Machine Learning, Jun. 5, 2017, accessed Dec. 22, 2022, www.towardsdatascience.com/cross-validation-in-machine-learning-72924a69872f.

Hussain, et al, A Healthcare Digital Twin for Diagnosis of Stroke, 2021 IEE International Conference on Becithcon, Dec. 4, 2021.

Information Communication in related International Application No. PCT/US2023/060120, dated Jan. 22, 2024, 2 pages.

International Preliminary Report on Patentability in related International Application No. PCT/US2023/060120, dated Apr. 24, 2024, 9 pages.

International Search Report and Written Opinion of the International Searching Authority in related International Application No. PCT/US2023/060120, dated May 12, 2023, 20 pages.

Invitation in related International Application No. PCT/US2023/060120, dated Jan. 31, 2024, 5 pages.

Kaur, et al, Early Stroke Prediction Methods for Prevention of Strokes, Behavioural Neurology, Apr. 11, 2022, 9 pages.

Korotchikova, et al, Quantitative EEG analysis in neonatal hypoxic ischaemic encephalopathy, Clinical Neurphysiology, vol. 122 No. 8, Dec. 18, 2010, 8 pages.

Lim, Y , Stacked Ensembles—Improving Model Performance on a Higher Lever, accessed Dec. 21, 2022, www.towardsdatascience.com/stacked-ensembles-improving-model-performance-on-a-higher-level-99ffc4ea5523.

Mainali, et al, Machine Learning in Action: Stroke Diagnosis and Outcome Prediction, Frontiers in Neurology, Dec. 6, 2021, 16 pages.

Meenen, et al, Detection of Large Vessel Occlusion Stroke in the Prehospital Setting, Jul. 2021, 9 pages.

Melgaard, et al, Assessment of the CHA2DS2-VASc Score in Predicting Ischemic Stroke, Thromboembolism, and Death in Patients With Heart Failure With and Without Atrial Fibrillation, accessed Aug. 26, 2022, www.jamanetwork.com/journals/jama/fullarticle/2431702?resultClick=1.

Park, et al, Quantitative Analysis of EEG Power Spectrum and EMG Median Power Frequency Changes after Continuous Passive Motion Mirror Therapy System, Sensors, Apr. 21, 2020, 16 pages.

Response Under Rule 66 in related International Application No. PCT/US2023/060120, dated Mar. 19, 2024, 15 pages.

Wijaya, et al, Electroencephalography (EEG) for Detecting Acute Ischemic Stroke, 2015 4th International Conference on ICICI-BME, IEEE, Nov. 2, 2015, 4 pages.

Wilkinson, et al, Predicting stroke severity with a 3-min recording from the Muse portable EEG system for rapid diagnosis of stroke, Scientific Reports, Oct. 28, 2020, 11 pages.

Funda Gunes et al. Stacked Ensemble Models for Improved Prediction Accuracy, SAS Institute, Inc., Jan. 1, 2017, 19 pages.

Kumar, EEG Classification for Stroke Detection Using Deep Learning Networks, IEEE Conference, Jun. 24-25, 2022, Abstract, 1 page.

\* cited by examiner

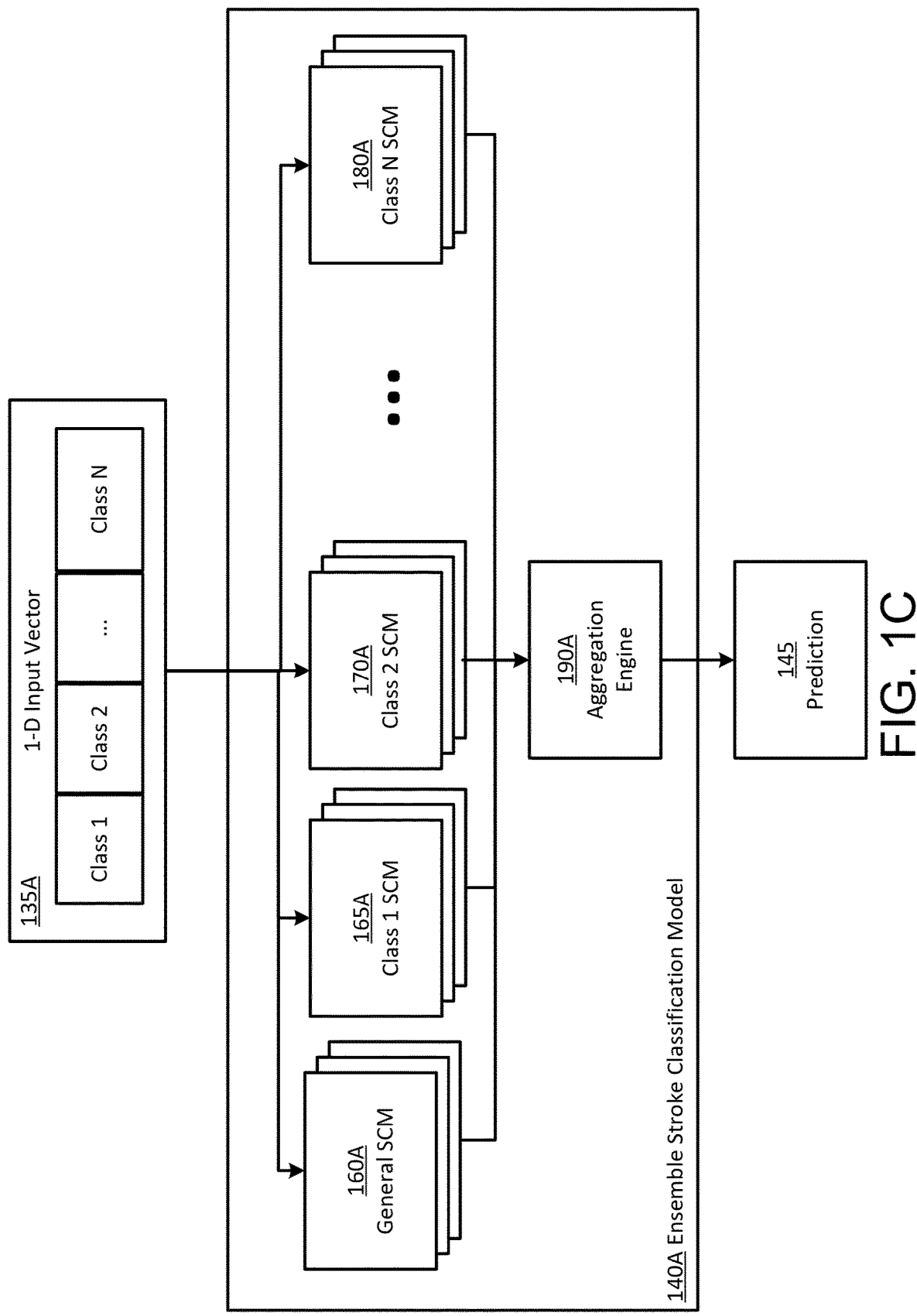

STROKE PREDICTION MULTI-ARCHITECTURE STACKED ENSEMBLE SUPERMODEL

CROSS-REFERENCE TO RELATED APPLICATIONS

This application claims the benefit of U.S. Provisional Application Ser. No. 63/266,448, titled "Field Detection of Large Vessel Occlusion Stroke," filed by Krag Browder, on Jan. 5, 2022, and the benefit of U.S. Provisional Application Ser. No. 63/266,449, titled "Field Detection of Large Vessel Occlusion Stroke," filed by Krag Browder, on Jan. 5, 2022.

This application incorporates the entire contents of the foregoing application(s) herein by reference.

TECHNICAL FIELD

Various embodiments relate generally to stroke detection.

BACKGROUND

Occlusion of vasculature (e.g., blood vessels) may lead to stroke. For example, stroke may be caused by occlusion of blood vessels feeding one or more portions of the brain and/or other portions nervous system. Electroencephalogram (EEG) may primarily be used to diagnose seizures and manage epilepsy. It has been used to monitor cerebral ischemia, particularly in the intraoperative setting during carotid artery surgery and, more recently, in acute ischemic stroke.

SUMMARY

Apparatus and associated methods relate to emergency stroke detection and classification. In an illustrative example, a stroke detection device may include an ensemble stroke classification model (ESCM). The ESCM may, for example, include class-specific model sets applicable for at least four classes of features, and a general model set applicable for all classes of features. Each model set, for example, may be stacked with multiple class-specific models for each of a corresponding group of architectures. The stroke detection device may, for example, extract predetermined features from a rolling window of a first predetermined duration of EEG data. The predetermined features are extracted and combined into a 1-D input vector. By applying the input vector, the stroke detection device may generate a binary stroke prediction result. Various embodiments may advantageously accurately predict whether a patient is experiencing a stroke within a finite time to assist an emergency service personnel.

Various embodiments may achieve one or more advantages. For example, some embodiments may advantageously predict LVO stroke. Some embodiments, for example, may include an accuracy of more than 85%. For example, some embodiments may train the ESCM with randomly selected windows in training data to advantageously reduce bias. Some embodiments may advantageously include EEG detection headset with leads locating on main brain arteries. Some embodiments may, for example, advantageously enable emergency personnel to use the stroke detection device with minimal training.

The details of various embodiments are set forth in the accompanying drawings and the description below. Other features and advantages will be apparent from the description and drawings, and from the claims.

BRIEF DESCRIPTION OF THE DRAWINGS

FIG. 1C is a block diagram depicting an exemplary ensemble stroke classification supermodel (ESCS) in a second embodiment.

Like reference symbols in the various drawings indicate like elements.

DETAILED DESCRIPTION OF ILLUSTRATIVE EMBODIMENTS

Figure 1A:
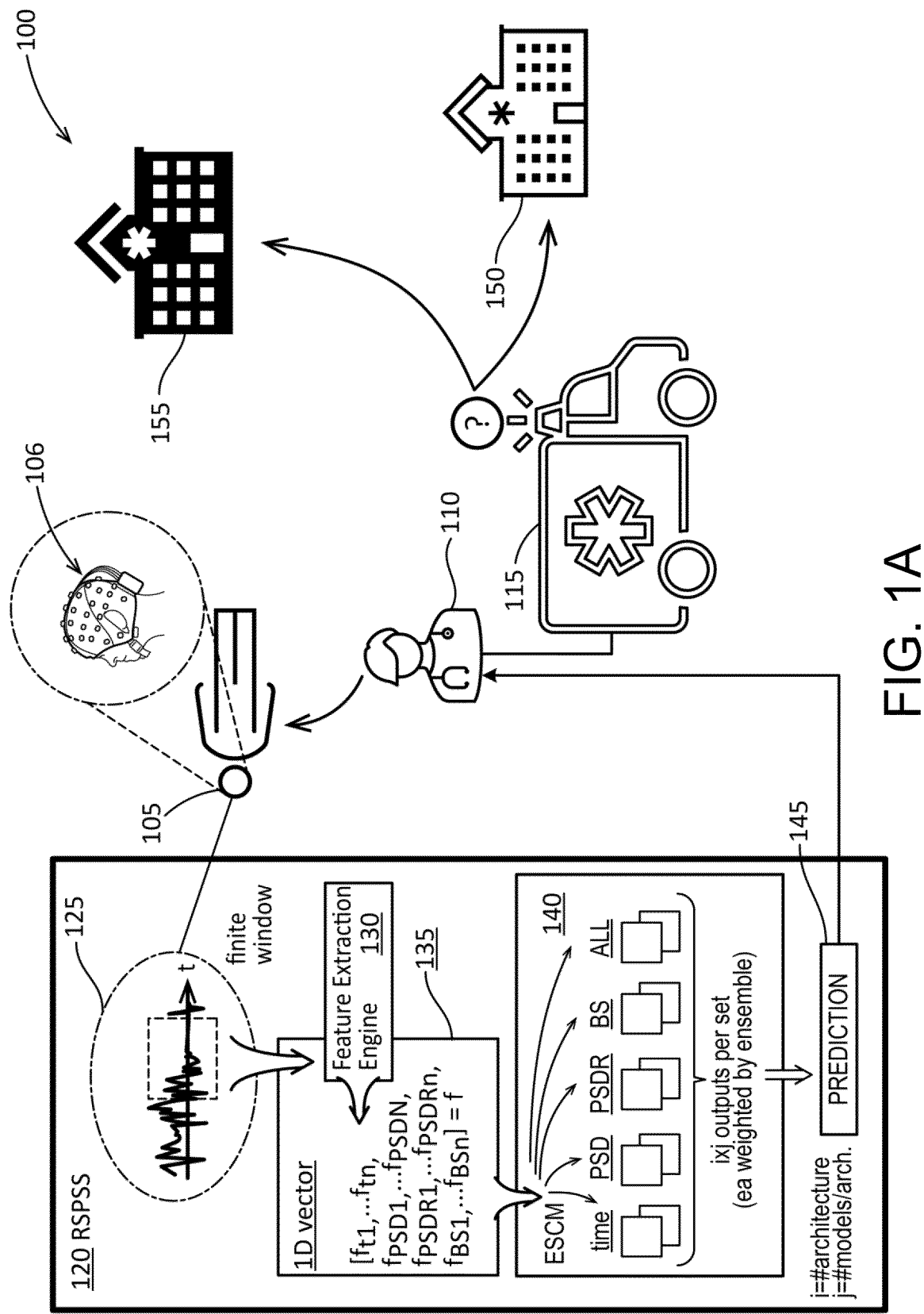
FIG. 1A depicts an exemplary stroke prediction supermodel system (SPSMS) employed in an illustrative use-case scenario.

To aid understanding, this document is organized as follows. First, to help introduce discussion of various embodiments, a field stroke classification system (FSCS) is introduced with reference to FIGS. 1-3. Second, that introduction leads into a description with reference to FIGS. 4-6, this document describes exemplary apparatus and methods useful for training, using, and designing the FSCS. Third, with reference to FIGS. 7-8E, exemplary EEG measurement headsets are described in application to exemplary EEG data collection in the FSCS. Finally, the document discusses further embodiments, exemplary applications and aspects relating to ensemble classification models applicable for monitoring and diagnosis.

Stroke is the second leading cause of death and the primary cause of long-term disability worldwide costing the US $65B every year. Nearly 800,000 people suffer from a stroke in the US annually and 40% are left with a permanent disability. There may be a single variable that correlates strongest with permanent disability and mortality: time. A study of nearly 7,000 stroke patients indicated that the average onset-to-intervention time was nearly 4 hrs, with the best outcomes achieved under three hours and statistically significant improvements for each 15-minute window under that threshold. While interventions, if given in a timely manner, may reduce long-term disability, not all interventions work for different types of strokes. 87% of strokes are ischemic in nature (AIS) but administering anti-coagulants to the 13% of hemorrhagic stroke patients would be disastrous. Within AIS, 46% of patients suffer a large vessel occlusion (LVO) which greatly benefits from endovascular therapy (EVT), but the risk associated with this procedure outweighs the benefits until an LVO can be confirmed.

Public health impact of EVT may be highly dependent on rapid identification of severe stroke symptoms by emergency medical services (EMS) personnel and transport to a comprehensive stroke center (CSC) with experience in providing fast, effective, and safe interventions. Despite major therapeutic improvement, only a limited number of hospitals are EVT capable. While changes in EEG signals can reliably be detected in AIS the practical application of these in the pre-hospital setting has been previously nearly non-existent owing to two major issues: 1) Form factor and time to data collection, and 2) Requisite off-line, manually intensive data analysis. Dense electrode arrays with >250 leads that require electroconductive gels may, for example, not be practically deployable in the prehospital setting due to high training requirements and long setup times to acquisition. Furthermore, once the data is collected, artifacts need to be removed and the salient features that are predictive of LVO need to be extracted and integrated into a model to make a determination. EMS personnel are not data scientists. Various embodiments may advantageously provide a technical solution to such technological problems. For example, the technical solution may advantageously provide an automatic, field-deployable process with high accuracy.

FIG. 1A depicts an exemplary stroke prediction super-model system (SPSMS) employed in an illustrative use-case scenario. In a prehospital setting scenario 100, a patient 105 is being assisted by an EMS personnel 110 in a pre-hospital setting. For example, the patient may be having a medical emergency. For example, the EMS personnel 110 may be an emergency medical technician (EMT). For example, the EMS personnel 110 may be an emergency room doctor. For example, the EMS personnel 110 may be a nurse. For example, the patient 105 may be seeking medical care because of suspicion of a stroke.

In some examples, the goal of EMS personnel 110 may be quickly triage of the patient 105 in order to 1) confirm a suspected stroke and 2) identify the most probably stroke type in order to either start an intervention while en route to the hospital or route the patient 105 by an ambulance 115 to a stroke center that has the capability to administer EVT. In this example, the EMS personnel 110 may use a SPSMS 120 to help decide whether the patient 105 is experiencing a stroke. For example, the SPSMS 120 may be installed in the ambulance 115. For example, the SPSMS 120 may be operable when the ambulance 115 is en route to a hospital. In some implementations, the SPSMS 120 may also generate a result to predict a type of stroke that the patient 105 is experiencing.

The SPSMS 120 may, as shown, receive EEG data 125 from the patient 105. For example, the SPSMS 120 may receive the data by a portable EEG headset. In some embodiments, the EEG data 125 may be collected by an arrangement of dry electrodes (e.g., that may not require conductive gels) at fixed positions within a malleable headset. Various embodiments may be hardware agnostic, which may provide flexibility to users to utilize EEG hardware of their choice.

In some implementations, the SPSMS 120 may receive a short (e.g., 3 minutes) finite window of EEG data 125 from the patient 105. For example, the duration of the finite window may be predetermined (e.g., by a manufacturer of a RSPSS, an organization of the EMS personnel 110). As shown, a feature extraction engine (FEE 130) receives the window of EEG data 125. For example, the FEE 130 may identify and aggregate the received EEG data 125. For example, the identified features may include time-series features, frequency domain features (e.g., power spectrum density (PSD), PSD ratio), and other computed features (e.g., brain symmetry, Intra region symmetry).

In some implementations, the FEE 130 may include an automated real-time artifact elimination and feature extraction algorithm. Artifacts may, by way of example and not limitation, arise from a number of sources including blinks, oculomotor movements, and/or physical disturbance of the electrodes (this is perhaps especially true in the pre-hospital setting when patients are in a moving ambulance). In order to create an accurate classification system, these may need to be removed and salient features extracted that provide predictive value.

In various embodiments, a deep learning model may be configured to discriminate LVO in patients with AIS from historical datasets. In various embodiments, the model may, for example, be validated by collecting clinical data with a portable EEG. Two separate clinical data collection sites may, for example, be utilized to generate data from at least 50 LVO cases as a proof-of-concept. The accuracy (combination of sensitivity and specificity) of the system may, for example, be assessed in two classification models: stroke vs non-stroke and LVO vs non-LVO targeting an accuracy of 80%. Receiver Operating Characteristic (ROC) curves may, for example, be produced targeting an area under the ROC curve (AUC) of greater than 0.95.

Following the artifact removal, the next step of data pre-processing before model development may be to extract salient features from the time-series data that have high predictive value for delineating stroke vs control and LVO vs non-LVO patients. Primary candidates may, for example, include the brain symmetry index (BSI), an EEG feature measure of interhemispheric differences, specific asymmetry BSI, and rhythmic ratios such as DAR (delta/alpha) and DTABR ((delth+theta)/(alpha+beta)). In addition to these features, various embodiments may examine non-linear features including permutation entropy (PerEn) and fractal dimension (FD) (e.g., to test the degree of irregularity and complexity, which may show significant changes in patients with VaD and stroke-related MCI than that in control subjects).

The FEE 130 may, in the depicted example, aggregate the identified features into an one-dimensional (1-D) input vector 135. For example, the 1-D input vector may, in some implementations, feed into an ensemble stroke classification model (ESCM 140) to determine (or predict) whether the patient is having a stroke. The ESCM 140 may, for example, be referred to as a stacked ensemble stroke classification model (SESCM). In some implementations, the ESCM 140 may include stacked class-specific models for each classification of features (e.g., time-series features, frequency domain features (e.g., power spectrum density (PSD), PSD ratio), and other computed features (e.g., brain symmetry, Intra region symmetry). In various implementations, the ESCM 140 may include stacked generic classification models for general (overall) features.

In some implementations, the ESCM 140 may include, for each classification of features, a corresponding group of architectures. For example, the corresponding group of architectures may be specialized to effectively be applied to a specific classification of features. In some implementations, each class-specific model may be configured to receive the 1D input vector 135 and operate on features of the corresponding class. In some implementations, the generic model may be configured to receive the 1D vector 135 and operate on features of multiple classes. For example, each of the models of the ESCM 140 may include supervised classification or supervised learning models to build a binary classification model.

The output of each of the models may generate, for example, a binary classification of whether a stroke exists in the patient 105. Based on a predetermined weighted aggregation of an output of each of the class-specific models and each of the general models, in this example, the ESCM 140 may generate a final prediction 145. In some implementations, the final prediction 145 may be a binary prediction of whether a LVO stroke is present or absent. In some implementations, the final prediction 145 may include a probability prediction of a presence of a stroke (e.g., in a scale of 0-1 or 0%-100%).

In some implementations, the final prediction 145 may be generated in near real-time. For example, after the SPSMS 120 receives a rolling window of EEG data 125 of a predetermined duration (e.g., 2 minutes, 3 minutes, 5 minutes, 10 minutes of data), the SPSMS 120 may generate the final prediction 145 in near time. For example, the SPSMS 120 may generate the final prediction 145 within 6 hours. For example, the SPSMS 120 may generate the final prediction 145 within 2 hours. For example, the SPSMS 120 may generate the final prediction 145 within 30 minutes. For example, the SPSMS 120 may generate the final prediction 145 within 10 minutes. For example, the SPSMS 120 may generate the final prediction 145 within 3 minutes. For example, the SPSMS 120 may generate the final prediction 145 within 20 seconds.

As an illustrative example as depicted, the EMS personnel 110 may decide whether to route the patient 105 to a closer hospital 150 or a stroke center hospital 155 based on the final prediction 145. For example, the stroke center hospital 155 may be EVT-capable, but it is further away. Normally, for example, the EMS personnel 110 may direct the ambulance 115 to the closer hospital 150 based on proximity. However, if the patient 105 is confirmed to be experiencing a stroke at the closer hospital 150, the closer hospital 150 may have to transfer the patient 105 to the 155 due to lack of correct equipment to treat the patient 105. For example, accordingly, to determine whether a patient has an LVO in the prehospital setting scenario 100 may advantageously enable routing to a facility that can provide the care needed.

In some embodiments, the final prediction 145 may have an accuracy of over 85%. In some implementations, the SPSMS 120 may provide a technical solution to a technical problem by providing an accurate, portable, and quick responding tool to the EMS personnel 110 to make a determination without the confirmation using complex and large equipment (e.g., tools for computerized tomography) within a hospital setting. Various embodiments may advantageously provide an EEG-based product for the EMS personnel 110 to use in a pre-hospital setting for fast and objective diagnosis of LVO in suspected stroke patients. In under five minutes, for example, various embodiments may enable EMS workers to deploy, collect data, and have the analyzed results presented in an intuitive dashboard identifying the probability of an LVO, advantageously enabling EMS workers to route patients en route to stroke centers with EVT capabilities. When a patient arrives at the hospital, the field determination made within the ambulance may, for example, be conveyed to physicians of the hospital. For example, having received the field determination, the physicals may immediately start intervention, reducing the time from onset to intervention and improving short and long-term patient outcomes. Without the accuracy of the final prediction 145, the physicians may have to delay the intervention by first diagnosing the patient 105 to generate a more accurate diagnosis, thereby possibly permanently reducing a chance of recovery of the patient 105. In some examples, if the delay is long enough, it may, for example, preclude the patient from receiving EVT altogether.

Accordingly, various embodiments may enable prehospital stroke identification to enable coordination with physicians to prepare for an incoming patient and/or eliminate the need for confirmation via computerized tomography (CT) angiography and/or other hospital-based imaging. For example, various embodiments may reduce a time to intervention and improve outcomes. Various embodiments may provide stroke identification that is both sensitive and specific, as false positives may, for example, result in missed opportunities for adequate treatment (e.g., Intravenous thrombolysis (IVT)).

Various embodiments may provide the EMS personnel 110 an objective tool to detect strokes that cannot be done in human minds. For example, the final prediction 145 may have a higher than 90% accuracy by utilizing extracted features in both time domain and frequency domain in a highly time sensitive environment. In some implementations, the ESCM 140 may also combine the final prediction 145 result with a professional prediction to advantageously further improve accuracy. For example, the EMS personnel 110 may determine a stroke classification according to a predetermined classification scale (e.g., Los Angeles Motor Scale (LAMS), National Institutes of Health Stroke Scale (NIHSS)). In some implementations, the predetermined classification scale may correlate a probability of a stroke occurring (e.g., likely, unlikely) and/or classification (e.g., stroke yes/no, type of stroke) based on physiological signs. By way of example and not limitation, physiological signs may include heart rate, body temperature, motor strength, speaking ability, and/or other qualitative features such as eye movements.

Figure 1B:
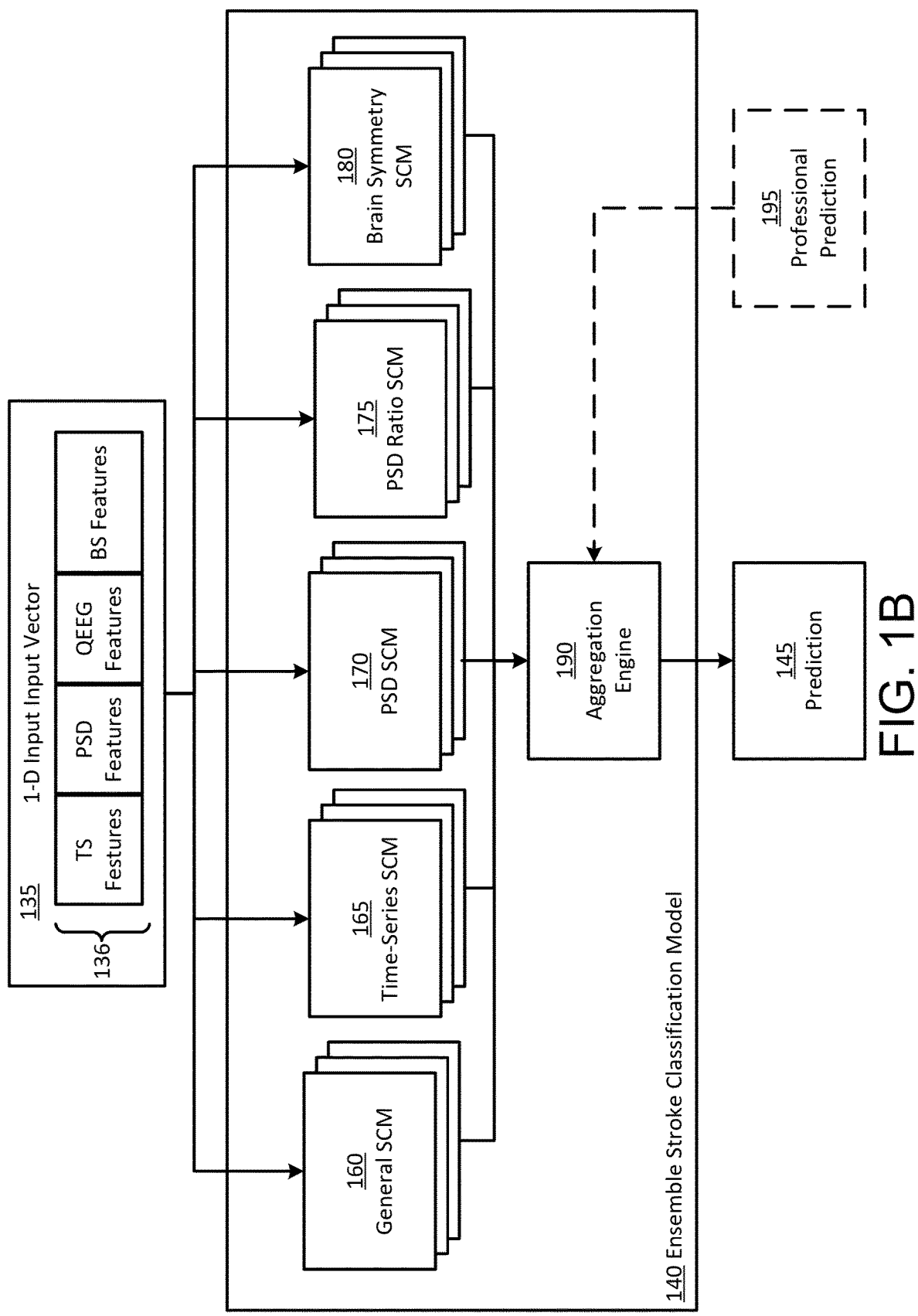
FIG. 1B is a block diagram depicting an exemplary ensemble stroke classification supermodel (ESCS).

FIG. 1B is a block diagram depicting an exemplary ensemble stroke classification supermodel (e.g., the ESCM 140 of FIG. 1A). As shown, the ESCM 140 includes stacked classification models (SCMs) for each specific set of classification features and for a general set of features (e.g., for all input). The ESCM 140 includes a general SCM 160, a time-series SCM 165, a PSD SCM 170, a PSD ratio SCM 175, and a brain symmetry SCM 180.

In some implementations, the SCMs 165, 170, 175, 180 for each classification of features may include multiple architectures (e.g., distributed random forest, gradient boosting model, deep neural network). For example, the multiple architectures included in the model sets may be predetermined based on an analysis of characteristics of the classification feature sets. In some implementations, each architecture for each classification features set may include multiple models. For example, the models may be selected qualitatively by analyzing heuristics of the features. For example, the models may be selected quantitatively by selecting, for example, 50 best performing models out of 100 models based on prediction results in a training session. For example, these models may be stacked to receive the same 1-D input vector 135 including multiple extracted features 136 ((e.g., to be represented by TS_Features, PSD_Features, QEEG_Features, and BS_Features, and the four classes of features may be integrated as ALL_Features).

In some implementations, the models may include distributed random forests, deep neural networks (DNNs), gradient boosting machines (GBMs), support vector machines, Generalized Linear Models (GLMs), Naive Bayes Classifiers (NBCs), extreme gradient boosting (XG-BOOST) classifiers, Light GBMs, and other supervised classification models. In some implementations, one or more of the SCMs 160, 165, 170, 175, 180 may be replaced by a single DNN. For example, the single DNN may be a convoluted recurrent DNN. In various implementations, subject to being trained by a large dataset correctly, a large convoluted DNN may provide a more accurate result. In some implementations, a SCM architecture may provide a highly accurate result with limited (e.g., realistically) available training data. For example, it may be unrealistic to obtain enough training EEG data with positive and negative prediction results from a large number of patients. Further discussion on training of the classification models is described with reference to FIGS. 3-4.

As shown, each of the SCMs 160, 165, 170, 175, 180 may each generate a prediction output to be received by an aggregation engine 190. The aggregation engine 190 may combine the prediction outputs to generate the final prediction 145. In some implementations, the aggregation engine 190 may combine the prediction outputs based on a weighted aggregation (e.g., based on a predetermined weighting factor for each model) of the prediction outputs. For example, the final prediction 145 may be a weighted average of the prediction outputs. In some implementations, the aggregation engine 190 may determine the weighting for each of the prediction outputs based on an optimization model against a highly specific cost function (e.g., to balance between specificity and sensitivity). In some embodiments, weightings used in the aggregation engine 190 may be trained using machine learning algorithms in a training session to be trained together with the SCMs 160, 165, 170, 175, 180. For example, in some implementations the aggregation engine 190 may be implemented as a meta-learner model.

In some implementations, the ESCM 140 may optionally combine the final prediction 145 result with a professional prediction 195 to advantageously further improve accuracy. For example, the EMS personnel 110 may determine a stroke classification according to a predetermined classification scale (e.g., Los Angeles Motor Scale (LAMS), National Institutes of Health Stroke Scale (NIHSS)). In some implementations, the predetermined classification scale may correlate a probability of a stroke occurring (e.g., likely, unlikely) and/or classification (e.g., stroke yes/no, type of stroke) based on physiological signs. By way of example and not limitation, physiological signs may include heart rate, body temperature, motor strength, speaking ability, and/or other qualitative features such as eye movements. The aggregation engine 190 may receive the professional prediction 195. For example, the aggregation engine 190 may combine the professional prediction 195 with other prediction outputs from the SCMs 160, 165, 170, 175 to generate the final prediction 145.

In some implementations, the ESCM 140 may be trained using a data bank of EEG. For example, each recording in the data bank may be accompanied by a brief clinical description of the patient's condition created by a physician at time of recording. Positive and negative labels were determined for stroke identification. For example, the clinical descriptions to identify recordings may include (AS—Acute stroke), (PAS—Past acute stroke, current EEG normal), (MCA—middle cerebral artery occlusion), (PMCA—Past MCA, current EEG normal), (ICA—Internal carotid artery occlusion), (PICA—Past ICA, current EEG normal), (ACA—Anterior Cerebral artery occlusion), (PACA—Past ACA, current EEG normal), (HC—Healthy EEG). "Past" refers to a previous history but no current presentation of symptoms. PAS, PMCA, PICA, PACA may be deliberately identified as to eliminate incorrect labels in the positive class.

In some implementations, a positive label may be associated with recordings of AS, MCA, ICA, and ACA. For the negative label, HC may be used. In some examples, minimum sensor configurations in the data may be calculated. For example, 30 configurations may be evaluated (e.g., manually) for sensor names. For example, a resulting 'minimum common sensor' set may include 19 sensors {'C3', 'C4', 'CZ', 'F3', 'F4', 'F7', 'F8', 'FP1', 'FP2', 'FZ', 'O1', 'O2', 'P3', 'P4', 'PZ', 'T3', 'T4', 'T5', 'T6'}. For example, sub-setting on these EEG channels may allow for subsequent use of the entire dataset of EEG recordings for feature engineering and model development.

In some implementations, during the training process, data cleaning is performed. For example, training recordings may include extremely noisy or zero variance at the beginning because of bad sensor connections. In some implementations, a random sampling method may be applied to the training recordings to generate samples of 3-minute windows of data beginning between the first and fifth minutes of each of the training recordings to advantageously prevent bias towards the distortion.

In various embodiments, the ESCM 140 may be trained to detect stroke vs non-stroke with an AUC≥0.95, specificity ≥95%, and/or sensitivity ≥65%. In some embodiments, a classifier may be configured to detect LVO vs non-stroke with an AUC≥0.80, specificity ≥80%, and/or sensitivity ≥65%.

FIG. 1C is a block diagram depicting an exemplary ensemble stroke classification supermodel (ESCS) in a second embodiment. In this example, an ESCM 140A may receive an 1-D input Vector 135A with N classes of features. The ESCM 140A includes a general SCM configured to use all the features in the vector 135A and, for each of the classes of features, a corresponding SCM (165A, 170A, 180A) for the specific class of feature.

The 140A includes an aggregation engine 190A to combine prediction outputs from each of the N SCMs. For example, the aggregation engine 190A may include N+1 weightings for each of the specific SCMs 165A, 170A, 180A (e.g., PSD_Features, QEEG_Features, TS_Features, and BS_Features) and the general SCM 160A (e.g., ALL_Features). For example, the sum of the weightings may be equal to 1. As shown, the final prediction 145 may be generated by the aggregation engine 190A.

Figure 2:
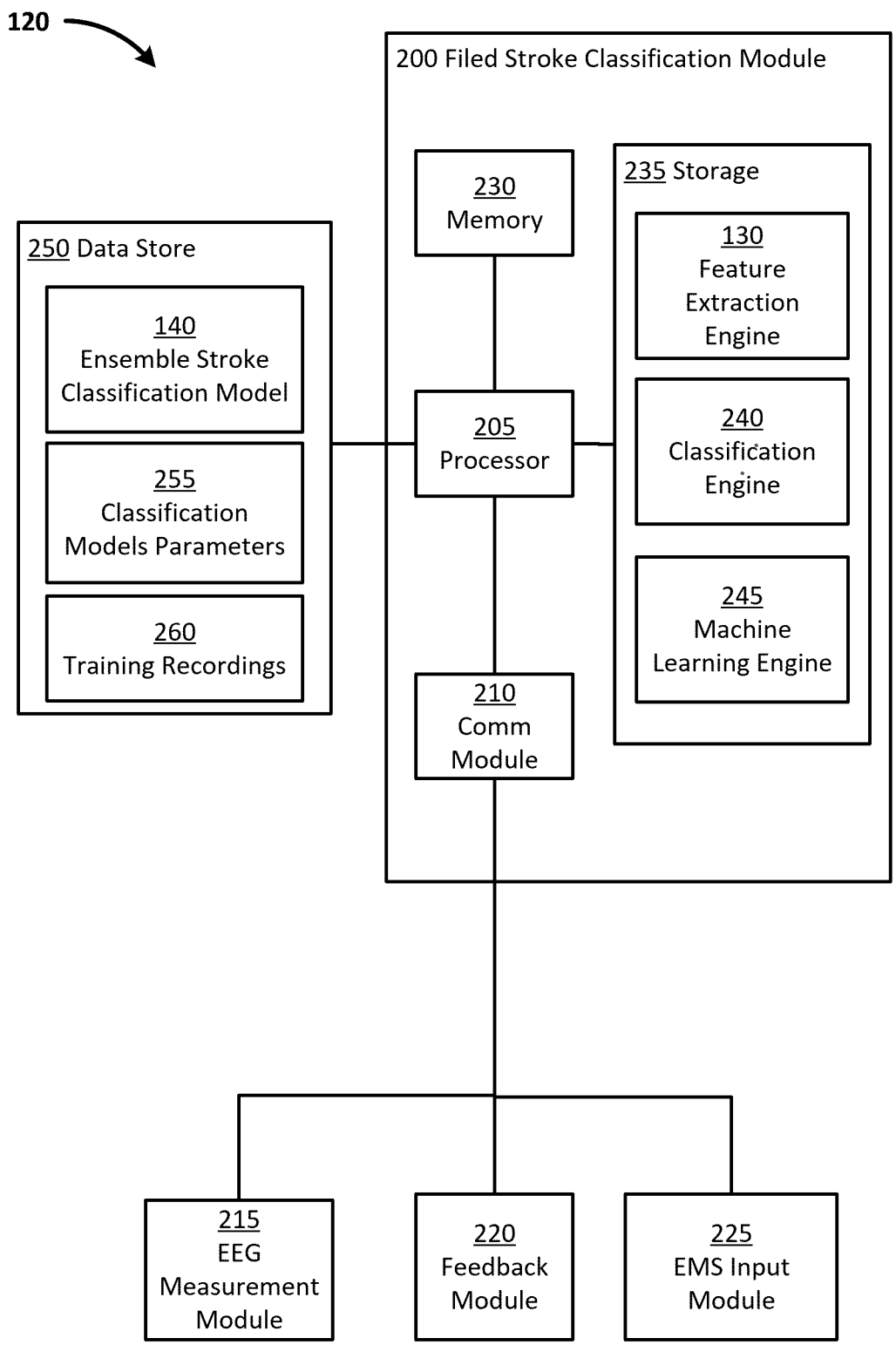
FIG. 2 is a block diagram depicting an exemplary SPSMS.

FIG. 2 is a block diagram depicting an exemplary SPSMS (e.g., the SPSMS 120). The SPSMS 120 includes a processor 205. The processor 205 may, for example, include one or more processing units. The processor 205 is operably coupled to a communication module 210. The communication module 210 may, for example, include wired communication. The communication module 210 may, for example, include wireless communication. In the depicted example, the communication module 210 is operably coupled to an EEG measurement module 215, a feedback module 220, and an EMS input module 225. The EEG measurement module 215 may be the portable headset (e.g., the headset 106), for example. The EEG measurement module 215 may, for example, receive a 3 minute rolling window of EEG data from the patient 105. The feedback module 220 may be configured to, for example, display an output of the SPSMS 120 and a status of the current diagnosis. For example, the feedback module 220 may generate an audio alert when the patient 105 is classified to be experiencing a stroke. The EMS input module 225 may, for example, allow the EMS personnel 110 to input observations (e.g., temperature, eye movement) of the patient 105. In some implementations, the EMS input module 225 may be a graphical user interface. In some examples, the EMS input module 225 may provide an input for the EMS personnel 110 to enter the professional prediction 195.

As an illustrative example, the headset 106 may be a Nautilus Research EEG Headset. For example, the headset 106 may be used to collect data (e.g., field data, validation data). In some implementations, the headset 106 may include dry EEG electrodes embedded into a neoprene cap. In some implementations, the collected data may be wirelessly transmitted. In various embodiments, users may, for example, choose a preferred collection hardware that fits their needs. Electrode positioning variability may, for example, be advantageously reduced by integration into a neoprene cap and conducting gels may not need to be applied to the head for data collection. Various embodiments may, for example, wirelessly transmit data to computing hardware of the user's choosing for analysis (e.g. tablet).

In some implementations, cranial accelerometry may be used to measure the headpulse as a tool to diagnose a LVO stroke. For example, headpulse may refer to nearly imperceptible head movements with each cardiac contraction cycle in response to blood flow forces transmitted via the carotid and vertebral arteries. For example, the headpulse of a patient may be measured using accelerometers in contact with the skull combined with electrocardiogram leads. Various embodiments of the headset 700 may advantageously provide field-deployed LVO detection that advantageously is usable in a traveling field setting. For example, some embodiments of a stroke prediction device including an ESCM may advantageously be housed in a portable housing (e.g., vehicle mounted, rolling, hand-carryable). Such embodiments may advantageously enable portable automatic stroke detection.

The processor 205 is operably coupled to a memory module 230. The memory module 230 may, for example, include one or more memory modules (e.g., random-access memory (RAM)). The processor 205 includes a storage module 235. The storage module 235 may, for example, include one or more storage modules (e.g., non-volatile memory). In the depicted example, the storage module 235 includes the FEE 130, a classification engine 240, and a machine learning engine 245.

The FEE 130 may receive EEG data from the patient 105 using the EEG measurement module 215, for example. The FEE 130 may generate PSD coefficients by calculating the EEG data's periodogram using the raw time domain EEG data and its sample frequency. In some implementations, from the periodogram, bins were created for each channel to obtain the normalized delta (0 to 3 Hz), theta (3 to 6 Hz), alpha (6 to 12 Hz), low beta (12 to 19 Hz), and high beta (19 to 30 Hz) frequency coefficients. These features, for example, may be the PSD class of features. The FEE 130 may also calculate Quantitative-EEG features, for example. The Quantitative-EEG features may include relative alpha percentage (RAP), relative alpha-beta percentage (RABP), relative delta-theta percentage (RDTP), delta/alpha ratio (DAR), delta-theta/alpha-beta ratio (DTABR), sum_psd_delta (SPD), sum_psd_theta (SPT), sum_psd_alpha (SPA), sum_psd_lowbeta (SPLB), sum_psd_highbeta (SPHB). From the time-series EEG data, for example, the FEE 130 may generate, for each sensor, a Shannon Entropy and Hurst Exponent. For example, these features may be categorized as the time-series features. To model the symmetric properties of the brain's signal, the FEE 130 may determine an Inter-Hemispheric Amplitude Ratio (IHAR) and a Brain Symmetry Index (BSI) as an aggregate index from all hemispheric sensor pairs. Additionally, BSI may, for example, be calculated for sensor pairs in each vascular region, including Posterior Cerebral Artery (PCA), Middle Cerebral Artery (MCA), and Anterior Cerebral Artery (ACA). For example, the FEE 130 may generate an input vector by combining the extracted features. In some implementations, the FEE 130 may clean the received EEG data by removing artifacts, extract salient features, and/or feed those extracted features into an advanced statistical model to generate a statistical probability of a stroke.

The classification engine 240, for example, may apply the ESCM 140 to the input vector 135 generated by the FEE 130. For example, the classification engine 240 may generate a binary prediction output indicating whether the patient 105 is experiencing a stroke. In some implementations, the classification engine 240 may be configured to specifically detect a probability of presence of LVO.

The machine learning engine 245 may, for example, include algorithms to train SCMs and the aggregation engine 190 of the ESCM 140. In some implementations, the machine learning engine 245 may be triggered periodically or by user selection to perform training on the ESCM 140. For example, the machine learning engine 245 may include a k-fold cross-validation function to advantageously prevent overfitting of the ESCM 140.

The processor 205 is further operably coupled to a data store 250. The data store 250 includes the ESCM 140, classification models parameters 255, and training recordings 260. For example, the classification models parameters 255 may include parameters specifically predetermined for each of the SCMs. For example, the classification models parameters 255 may include a depth of a random forest. For example, the classification models parameters 255 may include a selected classification model to be applied to a corresponding class of features. For example, the classification models parameters 255 may include a search space for a distributed random forest.

In some embodiments, the SPSMS 120 may perform stroke prediction classification automatically, for example, with no user input. Such embodiments may advantageously reduce training of the EMS personnel 110 required to use the SPSMS 120. For example, the EMS personnel 110 may quickly and efficiently triage the stroke, route patient to the best care setting possible, and/or transmit the information to the receiving medical care setting so that physicians can formulate a plan of care before the patient's arrival.

Various embodiments may, for example, be configured to be robust to differential hardware capabilities. For example, an LVO detection engine (e.g., including an analytics engine) may be configured to provide similar levels of accuracy using high density wet electrode arrays and/or low density dry electrodes. Various embodiments may, for example, be configured to use any hardware meeting (predetermined) minimum hardware requirements.

Figure 3:
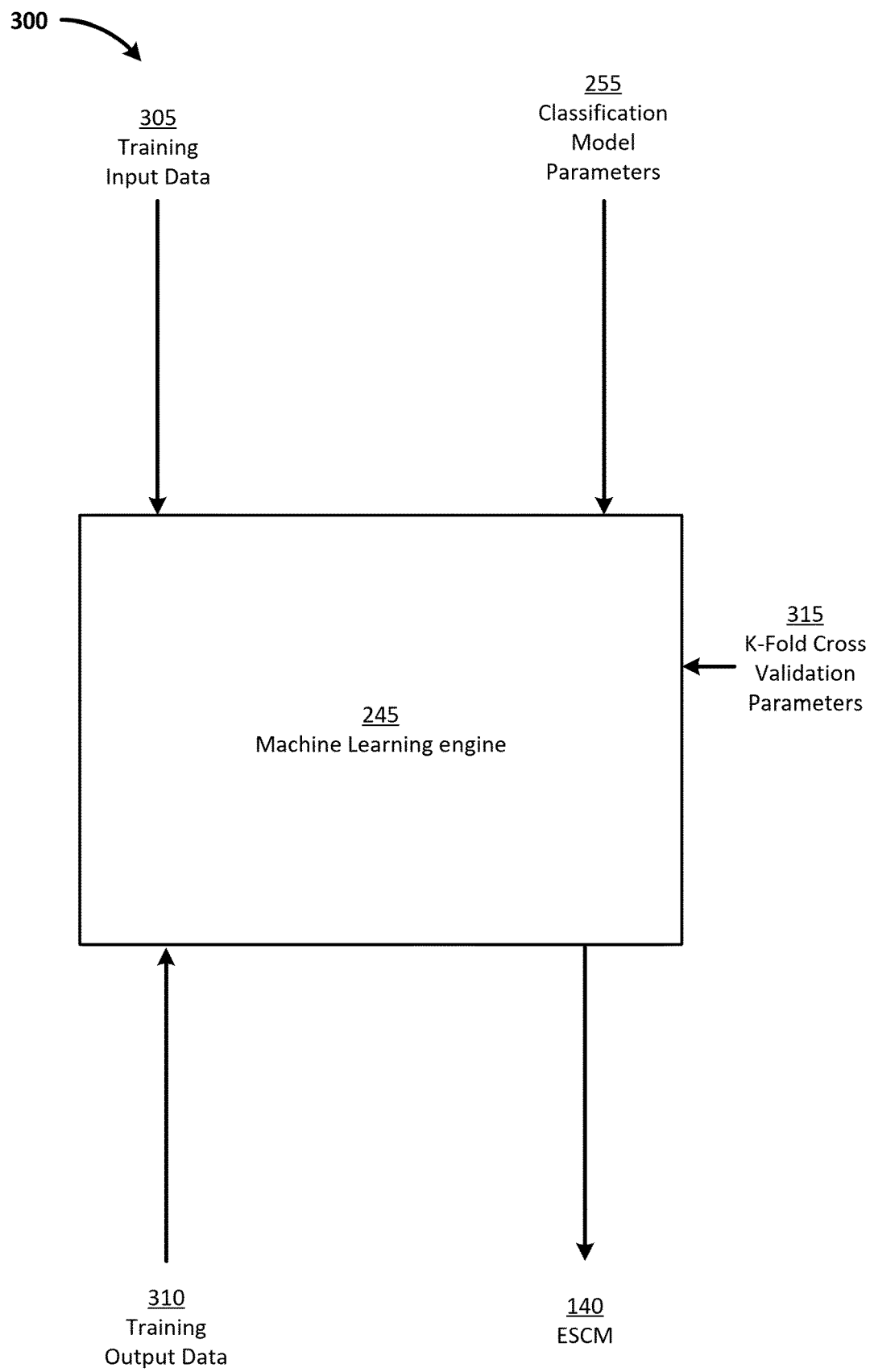
FIG. 3 depicts an exemplary machine learning engine for content characterization.

FIG. 3 depicts an exemplary machine learning engine for stroke prediction. In an exemplary scenario 300, the machine learning engine 245 includes a machine learning model. The machine learning model may, by way of example and not limitation, include a DRF, a DNN, a GBM, and other supervised classification model.

A set of training data is applied to the machine learning engine 245 to train the machine learning model. The training data includes a set of training input data 305 and a set of training output data 310. The set of training input data 305 may include historical EEG data recordings. The training input data 305 may include, for example, 1-D input vectors generated from a databank of the training recordings 260.

The set of training output data 310 may include, corresponding to each of the input vectors, positive and negative labels determined for stroke identification (as described with reference to FIG. 1B). As an illustrative example, the training input data may be generated based on a k-fold cross validation parameter 315. As an illustrative example, the training input data may be selected by randomly sampling at the first predetermined duration (e.g., the three minute finite window) from the training recordings 260 of at least a second duration longer than the first predetermined duration (e.g., from at least 10-minute long training recordings). For example, the ESCM may automatically train based on the training input data 305 until the ESCM is above an accuracy threshold and below an error threshold based on the k-fold cross validation parameter 315.

In some implementations, based on the k-fold cross validation parameter 315, each SCM may, for example, be created by training N models until a predetermined criterion is reached, and selecting from the N models a predetermined M number of models (where M<N) as the classification-specific model set, the M models having a closest result to a quality criterion.

In some embodiments, before training, random sets of testing data (derived from the training recordings 260 randomly) may be divided from the training data based on k-fold cross validation parameter 315. After the machine learning engine 245 is trained, the testing data may be applied to the trained model to test the training accuracy of the model. For example, the trained model may receive the testing input data and generate an output data in response to the testing input data. The generated output data may be compared with the testing output data to determine the prediction accuracy (e.g., based on a predetermined criterion(s) such as a maximum error threshold). In some embodiments, one or more models (e.g., neural network models) may be cascaded together. The cascaded model may be trained and tested. During operation, the classification models parameters 255 may be provided as inputs to the machine learning engine 245. The machine learning engine 245 may generate SCMs based on the classification models parameters 255 to be trained.

In an illustrative example, the k-fold cross validation parameter 315 may be three and may specify that the training data was randomly split into 80 percent training and 20 percent test ratio. The 80 percent training set may be, for example, used to construct an ESCM 140. The ESCM 140 may include the models selected based on a series of 3-fold cross validated grid searches for each class of feature types (e.g., PSD_Features, QEEG_Features, TS_Features, and BS_Features) plus a 3-fold cross validated grid search on the entire feature set (e.g., ALL_Features) based on the classification models parameters 255. For example, a logarithmic loss metric may be minimized during grid search to determine an optimal hyper-parameters of, for example, the aggregation engine 190. A Generalized Linear Model may be used as a meta-learner algorithm of the aggregation engine 190 to train the stacked ensemble, in some implementations.

For each category of features, in some implementations, a series of model types may be developed. For example, the TS_Features models may be a 3-folds cross-validated grid search collection of distributed random forests, gradient boosted machines and feed forward neural networks. The hyper-parameter grid for the random forest may, for example, search an optimal combination of number of trees (e.g., {200, 300, 350}). For example, a maximum depth of trees may be {20,21,22,23,24,25,26,30}. The classification models parameters 255 of an optimal gradient boosted machines may include a number of trees {200, 300, 350, 500}, a maximum depth of trees {10, 15, 20, 25, 30} and a learning rate {0.05, 0.07, 0.1, 0.2, 0.3}. The feed forward neural network's classification models parameters 255 may define the model architectures. For example, the number of nodes per hidden layer may be {[30,30,30,30,30], [30,30,30], [25,20,15], [15,10,8], and [12,12,12]}. The activation functions attempted may be set by the machine learning engine 245 as {hyperbolic tangent, rectified linear unit, rectified linear unit with dropout}. The number of maximum training epochs may be specified as [90, 105, 120, and 200], for example.

The PSD_Feature models may be created with a similar set of models as with the time series features and consisted of a 3-folds cross-validated grid search collection of distributed random forests, gradient boosted machines and feed forward neural networks. The random forest, for example, may include classification models parameters 255 may include grid parameters grid searched. For example, this may include a number of trees {200, 250, 300, 325, 350} and maximum depth of trees {20, 25, 30, 35}. The gradient boosted machine's grid parameters grid searched may include a number of trees {200, 300, 350, 500}, a maximum depth of trees {7, 10, 15, 20, 25, 30}, and a learning rate {0.009, 0.05, 0.07, 0.1, 0.2, 0.3}.

As an illustrative example, the QEEG_Features models may be built and assessed by 3-folds cross-validated grid search using a set of distributed random forests with predetermined classification models parameters 255. For example, the 255 may include a number of trees {125, 200, 250, 300} and a maximum tree depth {10, 15, 20, 25, 30}. For example, the ALL_Features model may be generated by 3-folds cross-validated grid search using a set of XGBoost models. For example, the classification models parameters 255 of the XGBoost models may include a number of trees {100, 125, 150, 250, 300, 350, 400} and a maximum depth {10, 15, 20, 25, 30, 35}.

In some implementations, the SCMs may be evaluated against a holdout test set to produce an Area Under the Receiver Operator Characteristic (AUROC) value of 0.89 and an Area Under the Precision-Recall curve (AUPRC) value of 0.91.

In some implementations, the machine learning engine 245 may generate SHAP (Shapley Additive exPlanitions) values of the test data to, for example, be calculated to provide a level of understanding and explainability to stroke classification decisions. Various embodiments may be configured to provide a clinician evaluating the stroke model with explainable predictive analytics.

Multiple (e.g., two, more than two) historical datasets may be included to train a fast and efficient algorithm to detect LVO from EEG data. This model may be validated (e.g., as above).

In various embodiments, an LVO detection engine (e.g., using a machine learning model(s)) may be configured, for example, to autonomously extract a multitude of features correlated with stroke with latency less than 15 seconds per 3-minute EEG sample.

In some embodiments, an LVO detection engine may be configured to use lasso regression modeling, for example, to naively select a subset of EEG variables.

Deep learning models may, for example, enhance the diagnostic capability of EEGs in the detection of AIS and LVO. Extreme Machine Learning (ELM), Support vector machines (SVM), k nearest neighbors (kNN), decision tree, and random forest classifiers may be, for example, implemented in some embodiments in the analysis of encephalographic stroke data. In some embodiments, one or more such models may be evaluated and/or included. For example, ensemble approaches may be included utilizing the pre-processed data. 20% of the dataset may, for example, in some embodiments be reserved for validation. Cross-validation may, for example, in some embodiments be part of generating the LVO detection engine model(s). The classification model may, for example, be assessed by calculating both type I and II errors (sensitivity and specificity) to generate an ROC curve with AUC calculated as the predominant performance metric. In some embodiments, two separate models may, by way of example and not limitation, be developed: stroke vs non-stroke, and LVO vs non-LVO.

Figure 4:
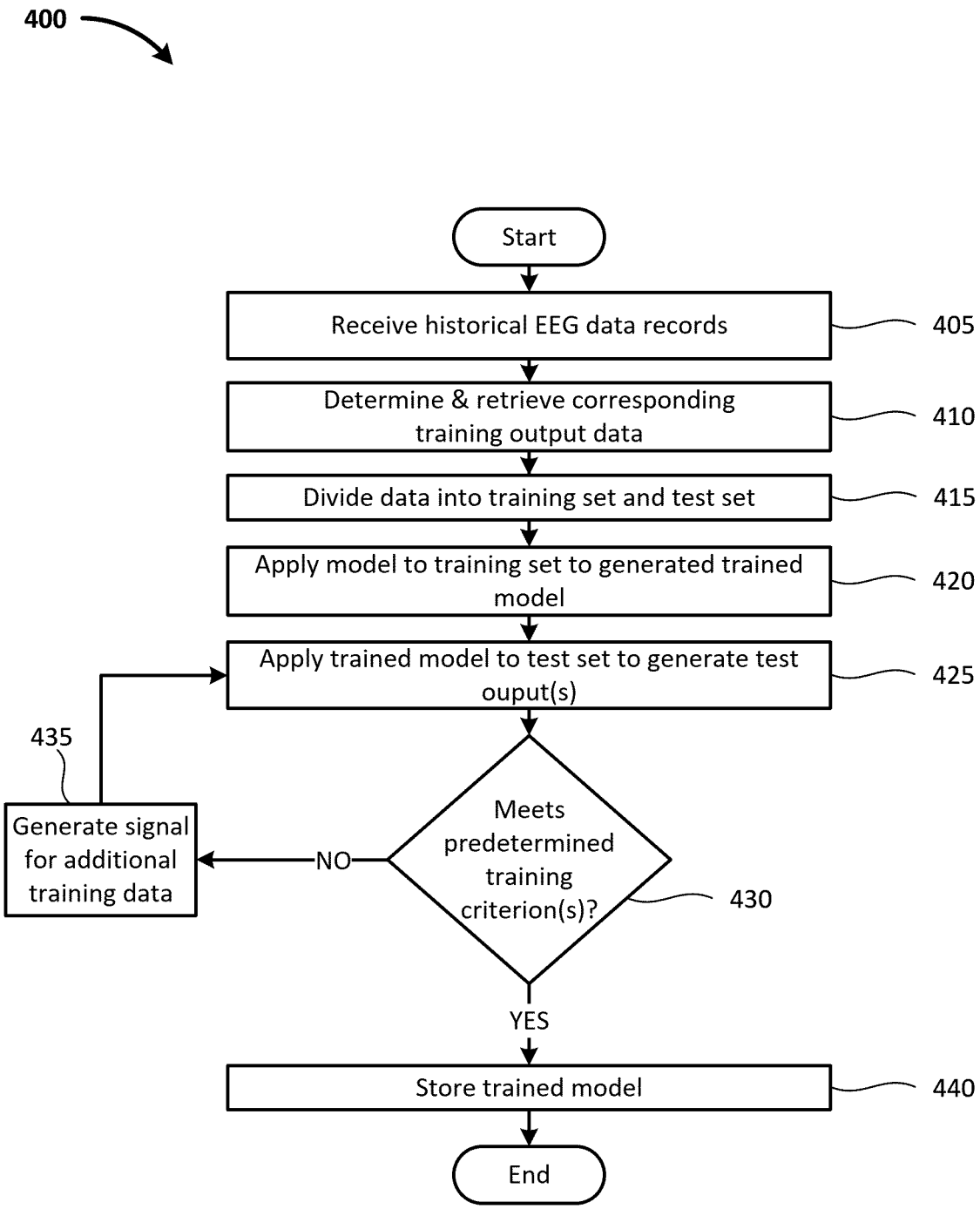
FIG. 4 depicts an exemplary method of training a classification model in an ESCM.

FIG. 4 depicts an exemplary method of training a ESCM. A method 400 may, for example, be performed by a processor(s) (e.g., processor 205) executing a program(s) of instructions retrieved from a data store(s) (e.g., storage module 235). For example, the machine learning engine 245 may execute the method 400 to train, within one of the SCM, one of the classification models (e.g., DRF, feed forward neural network). In some implementations, the method 400 may be part of a higher level machine learning method that incorporates iterations of training of each classification model in each SCM and a meta-learner model to combine output from all the classification models.

The method 400 includes, at a step 405, receiving historical EEG data records (e.g., the training recordings 260). At a step 410, corresponding training output data (e.g., the positive and negative classification labels corresponding to each of the training recordings 260) are determined and retrieved. For example, predetermined classification parameters (e.g., the classification models parameters 255 corresponding to a classification model under training, the k-fold cross validation parameter 315) are retrieved.

At a step 415, the retrieved data is divided into a first set of data used for training and a second set of data used for testing. For example, the division may be specified by the classification models parameters 255. At a step 420, a model is applied to the training data to generate a trained model (e.g., a DRF, a neural network model). The trained model is applied to the testing data, in a step 425, to generate test output(s) (e.g., stroke predictions). The output is evaluated, in a decision point 430, to determine whether the model is successfully trained (e.g., by comparison to a predetermined training criterion(s)). The predetermined training criterion(s) may, for example, be a maximum error threshold. The predetermined training criterion(s) may be maximum value of a cost function of sensitivity and specificity of the output. For example, if a difference between the actual output (the test data) and the predicted output (the test output) is within a predetermined range, then the model may be regarded as successfully trained. If the difference is not within the predetermined range, then the model may be regarded as not successfully trained. At a step 435, the processor may generate a signal(s) requesting additional training data, and the method 400 loops back to step 425. If the model is determined, at the decision point 430, to be successfully trained, then the trained model may be stored (e.g., in the data store 250), in a step 440, and the method 400 ends.

Figure 5:
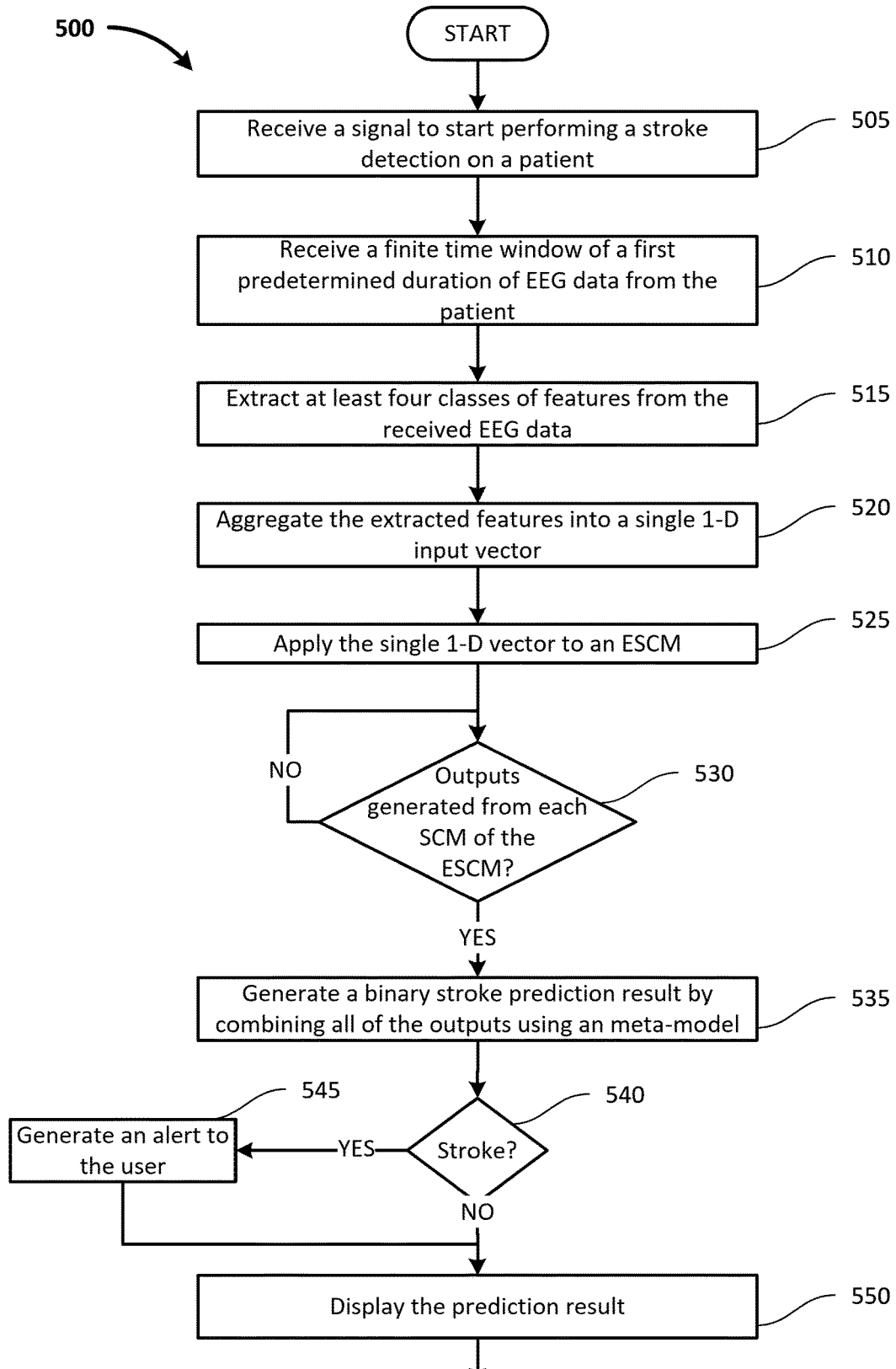
FIG. 5 is a flowchart illustrating an exemplary field patient stroke classification method.

FIG. 5 is a flowchart illustrating an exemplary field patient stroke classification method 500. For example, the exemplary field patient stroke classification method 500 may be performed by the SPSMS 120. For example, some steps may be performed by the FEE 130. Some of the steps may, for example, be performed by the classification engine 240. In this example, the method 500 begins when a signal to start performing a stroke detection on a patient is received in step 505. For example, the EMS personnel 110 may use the EMS input module 225 to transmit a signal to the SPSMS 120 to start analyzing whether the patient 105 is experiencing a stroke.

In step 510, a finite time window of a first predetermined duration of EEG data from the patient. For example, a three-minute rolling window of EEG data may be received from the headset 106. Next, in step 515, at least four classes of features from the received EEG data are extracted. For example, the FEE 130 may extract a time-series class feature, a PSD class feature, a quantitative EEG class feature, and a brain symmetry class feature from the EEG data 125.

In step 520, the extracted features are aggregated into a single 1-D input vector (e.g., the input vector 135). Next, the single 1-D vector is applied to an ESCM in step 525. For example, the classification engine 240 may apply the input vector 135 to the ESCM 140. In a decision point 530, it is determined whether outputs are generated from each SCM of the ESCM. For example, each of the classification models in the SCMs 160, 165, 170, 175, 180 may generate output at a different rate using the same input vector 135. If it is determined that not all outputs are generated from each SCM of the ESCM, the decision point 530 is repeated. If it is determined that all outputs are generated from each SCM of the ESCM, a binary stroke prediction result is generated by combining all of the outputs using a meta-learner model in step 535. For example, the aggregation engine 190 may combine the outputs from the SCMs 160, 165, 170, 175, 180.

In a decision point 540, it is determined whether a stroke is predicted. For example, a stroke may be predicted when the final prediction 145 is higher than a threshold (e.g., 0.5, 0.8). If there is a stroke, in step 545, an alert is generated to the user. For example, a warning sound may be generated using the feedback module 220. Next, the prediction result is displayed in step 550. For example, the feedback module 220 may also display the final prediction 145, and the method 500 ends. If it is determined that there is no stroke, the step 550 is performed.

Figure 6:
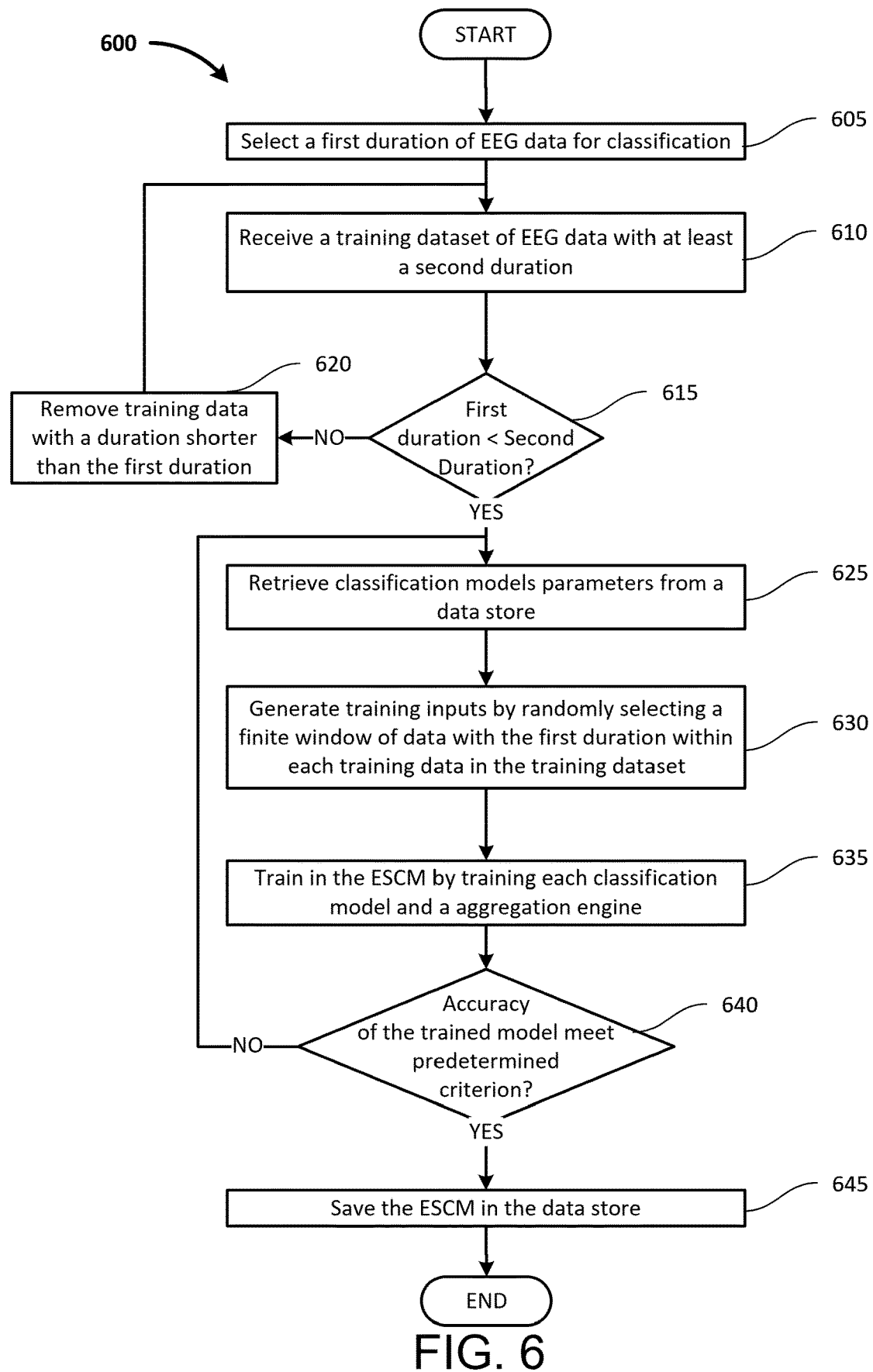
FIG. 6 is a flowchart illustrating an exemplary field patient stroke classification setup method.

FIG. 6 is a flowchart illustrating an exemplary field patient stroke classification setup method 600. For example, the SPSMS 120 may use the machine learning engine 245 to perform the exemplary field patient stroke classification setup method 600. For example, the SPSMS 120 may perform the method 600 during an initial setup of the SPSMS 120. For example, the SPSMS 120 may use the exemplary field patient stroke classification setup method 600 to calibrate a prediction accuracy.

In this example, the method 600 begins in step 605 when a first duration of EEG data is selected for classification. For example, the first duration may be selected to be a three-minute window. For example, the first duration may be selected to be a five-minute window. In some implementations, the first duration may be relatively short to advantageously enable quick analysis in the field by the EMS personnel 110.

In step 610, a training dataset of EEG data with at least a second duration is received. For example, the training recordings 260 may be received. In a decision point 615, it is determined whether the first duration is shorter than the second duration. If the first duration is not shorter than the second duration, in step 620, training data with a duration shorter than the first duration is removed, and the step 610 is repeated. If the first duration is shorter than the second duration, classification models parameters are retrieved from a data store in step 625. For example, the classification models parameters 255 may be retrieved from the data store 250. For example, the classification models parameters 255 may include a user selected number of models in each of the SCMs, a user selected types of model architecture in each of the SCMs, parameters (e.g., number of layer, depth, search space) of each model architecture, parameters for k-fold cross validation for training the model architecture.

In step 630, training inputs are generated by randomly selecting a finite window of data with the first duration within each training data in the training dataset. For example, the machine learning engine 245 may randomly select a finite window of data with the first duration within each training record to advantageously remove bias results from a specific timing within the training recordings 260. Next, in step 635, the ESCM is trained by training each classification model and an aggregation engine. For example, the machine learning engine 245 may perform the method 400 to each of the model architectures of each SCM, and the meta-learner model used by the aggregation engine 190.

In a decision point 640, it is determined whether an accuracy of the trained models meets predetermined criterion. For example, the predetermined criterion may be to detect stroke vs non-stroke with an AUC≥0.95, specificity ≥95%, and/or sensitivity ≥65%. If it is determined that the accuracy of the trained models meet predetermined criterion, the ESCM is saved in the data store in step 645, and the method 600 ends. %. If it is determined that the accuracy of the trained models does not meet predetermined criterion, the step 625 is repeated. For example, a new set of classification models parameters may be received to fine tune the training result.

Figure 7B:
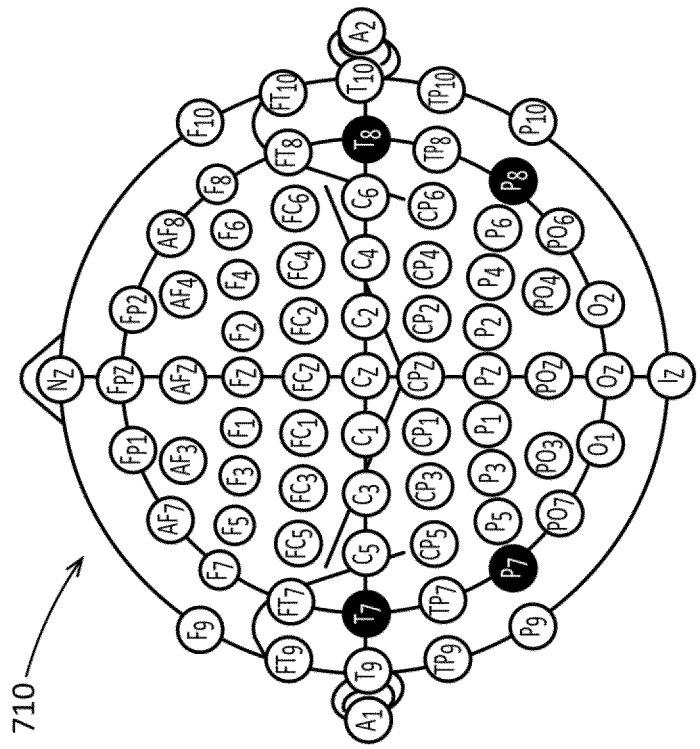
FIG. 7A, FIG. 7B, FIG. 7C, FIG. 7D, and FIG. 7E show correlations between positions of EEG headset leads with corresponding brain arteries.
Figure 7A:
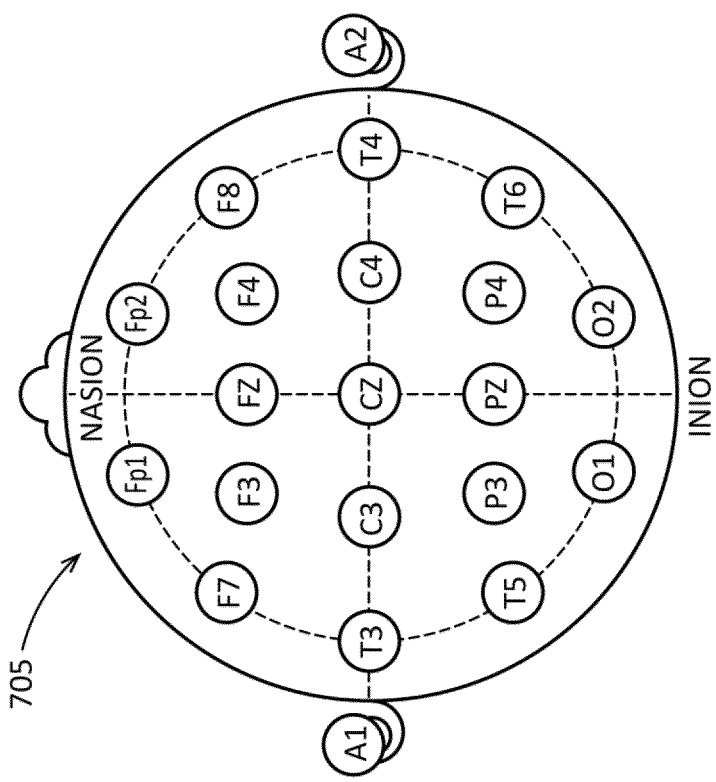
Figure 7C:
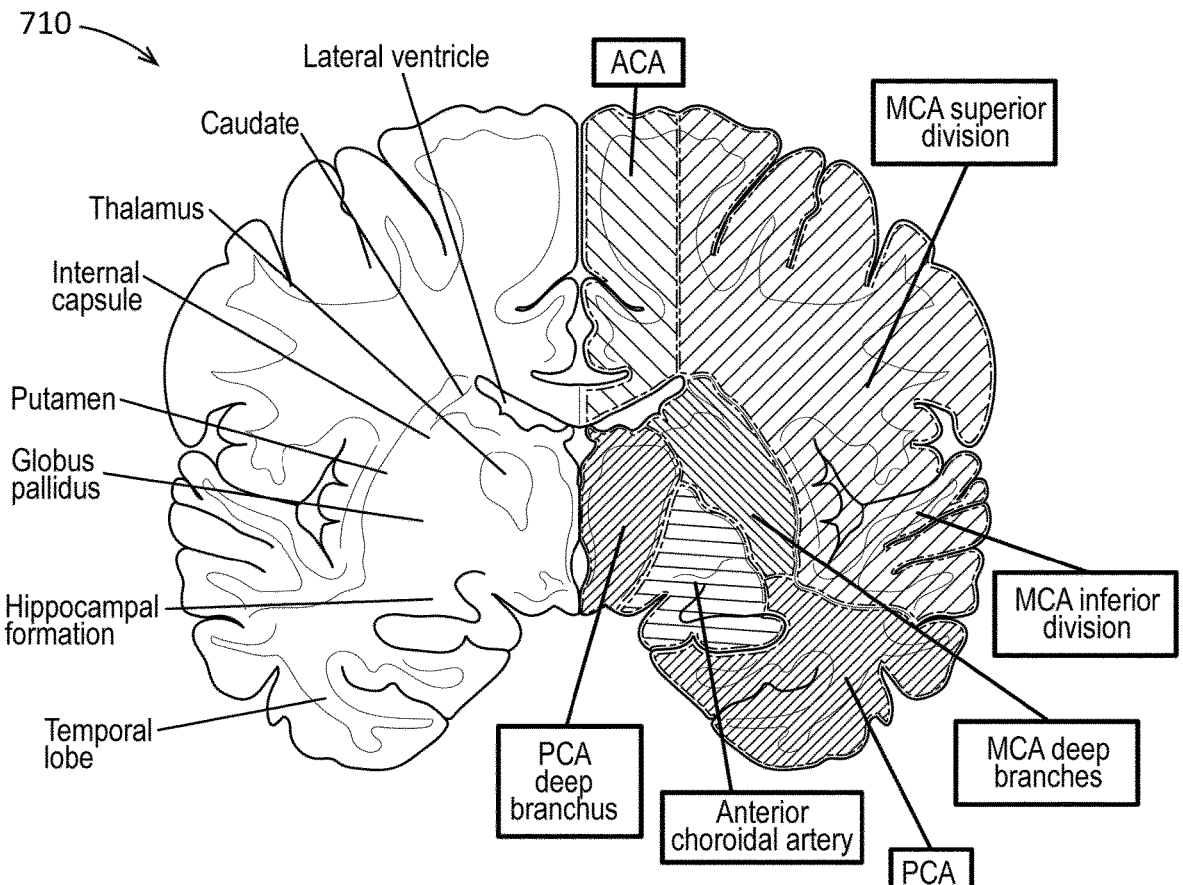
Figure 7D:
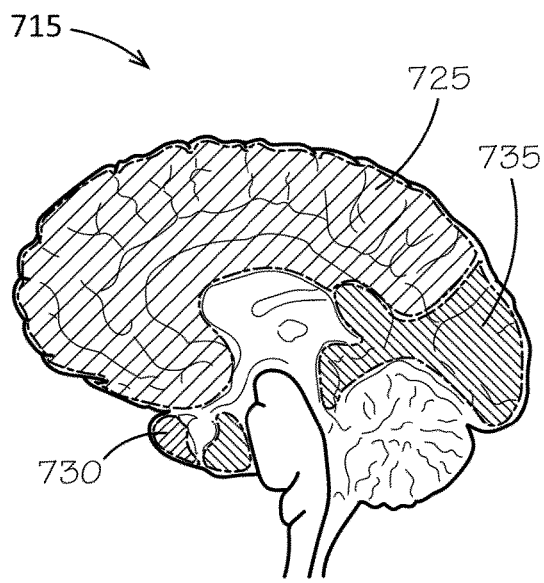
Figure 7E:
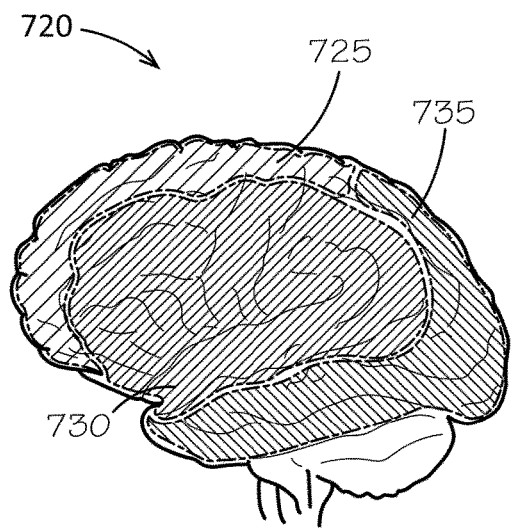

FIG. 7A, FIG. 7B, FIG. 7C, FIG. 7D, and FIG. 7E show correlations between positions of EEG headset leads with corresponding brain arteries. As shown in FIGS. 7A-7B, embodiments of a first EEG headset 700 and a second EEG headset 705 are shown. As shown in FIG. 7C-7E, main arteries of a brain are shown in a top view 710, a medial view 715, and a lateral view 720. In some implementations, the positions of various channels (leads) of a headset 700 may correlate with a corresponding artery. For example, as shown, the headset 700 includes a Fp1 correlates to a middle cerebral artery (MCA) channel, a Fp2 correlates to a MCA channel, a F7 correlates to a MCA channel, a F3 correlates to a MCA channel, a FZ correlates to an anterior cerebral artery (ACA) channel, a F4 correlates to a MCA channel, a F8 correlates to a MCA channel, a A1 correlates to a posterior cerebral artery (PCA) channel, a T3 correlates to a MCA channel, a C3 correlates to a MCA channel, a CZ correlates to an ACA channel, a C4 correlates to a MCA channel, a T4 correlates to a MCA channel, a A2 correlates to a PCA channel, a T5 correlates to a MCA channel, a P3 correlates to a MCA, PZ correlates to a PCA channel, a P4 correlates to a MCA channel, a T6 correlates to a MCA channel, a O1 correlates to a PCA channel, and a O2 correlates to a PCA. In some implementations, such as depicted, the PCA channel may include the PCA and the PCA deep branch(es).

As shown in FIGS. 7D-7E, a brain includes areas of ACA 725, MCA 730, and PCA 735. In some examples, EEG signals collected on a scalp may be a result of coordinated firing of neurons and neural activities. As a complex biological electricity signal, EEGs may have been indicated to reflect a functional state of the brain relating to a person's mental condition. For example, by extracting information from these signals, a patient's health may be diagnosed to identify different brain conditions.

Although various embodiments have been described with reference to the figures, other embodiments are possible.

In some implementations, the ESCM 140 may be a multi-classification model. For example, the ESCM 140 may include classification architecture to diagnose traumatic brain injuries (e.g., intracranial bleeding, subarachnoid hemorrhage). For example, by training the ESCM 140 using training recordings of diagnosing traumatic brain injuries, the SPSMS 120 may diagnose traumatic brain injuries.

In some implementations, by training the ESCM 140 using training recordings of tracking intracranial pressure, the ESCM 140 may include classification architecture to track intracranial pressure (e.g., to monitor whether ICP is rising).

In some implementations, by training the ESCM 140 using training recordings of post-lumbar puncture headache, the ESCM 140 may include classification architecture to diagnose post-lumbar puncture headache. In some implementations, by training the ESCM 140 using training recordings of Alzheimer's disease, the ESCM 140 may include classification architecture to detect Alzheimer's disease. In some implementations, by training the ESCM 140 using training recordings of complications of anesthesia, the ESCM 140 may include classification architecture to monitor and/or predict complications of anesthesia. In some implementations, by training the ESCM 140 using training recordings of dementia (e.g., front-temporal dementia), the ESCM 140 may include classification architecture to detect dementia. In some implementations, by training the ESCM 140 using training recordings of Parkinson's, the ESCM 140 may include classification architecture to detect Parkinson's.

In some implementations, by training the ESCM 140 using training recordings of Rehabilitation from stroke and/or brain injury, the ESCM 140 may include classification architecture to detect Rehabilitation from stroke and/or brain injury. For example, somebody lost use of a right arm. The ESCM 140 may generate a prediction\analytics of how much function they get back in their arm and track how much better it's getting. In some implementations, metrics may include looking at a size of abnormal signals over a motor cortex. For example, functional outcomes may be based on interventions. For example, the ESCM 140 may look at how it impacts a brain and use classes of features including analytics of brain mapping.

In some implementations, by training the ESCM 140 using training recordings of Multiple sclerosis, the ESCM 140 may include classification architecture to detect Multiple sclerosis. For example, the ESCM 140 may monitor response to therapeutics to predict where flare is going to occur (a predetermined demyelination, where the flare will occur, whether a patient responds to therapy).

In some implementations, by training the ESCM 140 using training recordings of Monitoring response to thrombolytics (e.g., TPA), the ESCM 140 may include classification architecture to detect Monitoring response to thrombolytics (e.g., TPA). In some implementations, by training the ESCM 140 using training recordings of Therapeutic outcomes and complications of EVT (endovascular surgery), the ESCM 140 may include classification architecture to detect Therapeutic outcomes and complications of EVT (endovascular surgery). In some implementations, by training the ESCM 140 using training recordings of Surgery complications, the ESCM 140 may include classification architecture to detect Surgery complications. In some implementations, by training the ESCM 140 using training recordings of complications of neurosurgery, the ESCM 140 may include classification architecture to detect complications of neurosurgery.

In some implementations, by training the ESCM 140 using training recordings of Anoxic brain injury, the ESCM 140 may include classification architecture to detect anoxic brain injury. In some implementations, by training the ESCM 140 using training recordings of Measuring response to medication, the ESCM 140 may include classification architecture to detect Measuring response to medication. In some implementations, by training the ESCM 140 using training recordings of Adverse events to medications, the ESCM 140 may include classification architecture to detect Adverse events to medications. In some implementations, by training the ESCM 140 using training recordings of Headache (including various subtypes), the ESCM 140 may include classification architecture to detect Headache (including various subtypes).

In some implementations, by training the ESCM 140 using training recordings of Brain malignancy, the ESCM 140 may include classification architecture to detect Brain malignancy. In some implementations, by training the ESCM 140 using training recordings of Elevated intracranial pressure, the ESCM 140 may include classification architecture to detect Elevated intracranial pressure. In some implementations, by training the ESCM 140 using training recordings of Hemorrhagic stroke, the ESCM 140 may include classification architecture to detect Hemorrhagic stroke. In some implementations, by training the ESCM 140 using training recordings of Chronic pain, the ESCM 140 may include classification architecture to detect Chronic pain. In some implementations, by training the ESCM 140 using training recordings of Myalgia, the ESCM 140 may include classification architecture to detect Myalgia. In some implementations, by training the ESCM 140 using training recordings of Psychiatric (schizophrenia, depression, anxiety), the ESCM 140 may include classification architecture to detect Psychiatric (schizophrenia, depression, anxiety). In some implementations, by training the ESCM 140 using training recordings of Essential Tremor, the ESCM 140 may include classification architecture to detect Essential Tremor. In some implementations, by training the ESCM 140 using training recordings of Lou-Gherig's disease (ALS), the ESCM 140 may include classification architecture to detect Lou-Gherig's disease (ALS).

Although an exemplary system has been described with reference to FIGS. 1A-C, other implementations may be deployed in other industrial, scientific, medical, commercial, and/or residential applications.

In various embodiments, some bypass circuits implementations may be controlled in response to signals from analog or digital components, which may be discrete, integrated, or a combination of each. Some embodiments may include programmed, programmable devices, or some combination thereof (e.g., PLAs, PLDs, ASICs, microcontroller, microprocessor), and may include one or more data stores (e.g., cell, register, block, page) that provide single or multi-level digital data storage capability, and which may be volatile, non-volatile, or some combination thereof. Some control functions may be implemented in hardware, software, firmware, or a combination of any of them.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an example of a system, which may be portable, has been described with reference to the above figures, other implementations may be deployed in other processing applications, such as desktop and networked environments.

Temporary auxiliary energy inputs may be received, for example, from chargeable or single use batteries, which may enable use in portable or remote applications. Some embodiments may operate with other DC voltage sources, such as 9V batteries, for example. Alternating current (AC) inputs, which may be provided, for example from a 50/60 Hz power port, or from a portable electric generator, may be received via a rectifier and appropriate scaling. Provision for AC (e.g., sine wave, square wave, triangular wave) inputs may include a line frequency transformer to provide voltage step-up, voltage step-down, and/or isolation.

Although particular features of an architecture have been described, other features may be incorporated to improve performance. For example, caching (e.g., L1, L2, . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades), and the like. One or more communication interfaces may be provided in support of data storage and related operations.

Some systems may be implemented as a computer system that can be used with various implementations. For example, various implementations may include digital circuitry, analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. Various embodiments may be implemented in a computer system that includes a graphical user interface and/or an Internet browser. To provide for interaction with a user, some implementations may be implemented on a computer having a display device. The display device may, for example, include an LED (light-emitting diode) display. In some implementations, a display device may, for example, include a CRT (cathode ray tube). In some implementations, a display device may include, for example, an LCD (liquid crystal display). A display device (e.g., monitor) may, for example, be used for displaying information to the user. Some implementations may, for example, include a keyboard and/or pointing device (e.g., mouse, trackpad, trackball, joystick), such as by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, the computers and networks forming the Internet, or some combination thereof. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, multiplexing techniques based on frequency, time, or code division, or some combination thereof. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

Various examples of modules may be implemented using circuitry, including various electronic hardware. By way of example and not limitation, the hardware may include transistors, resistors, capacitors, switches, integrated circuits, other modules, or some combination thereof. In various examples, the modules may include analog logic, digital logic, discrete components, traces and/or memory circuits fabricated on a silicon substrate including various integrated circuits (e.g., FPGAs, ASICs), or some combination thereof. In some embodiments, the module(s) may involve execution of preprogrammed instructions, software executed by a processor, or some combination thereof. For example, various modules may involve both hardware and software.

In an illustrative aspect, a stroke detection device (e.g., 120) may, for example, include a data store (e.g., 235) including a program of instructions. The data store may, for example, include a feature extraction engine (e.g., 130) configured to extract features from a rolling window of EEG data (e.g., 125) to generate a 1-D input vector (e.g., 135) of the extracted features (e.g., 136). The data store may, for example, include a classification engine (e.g., 240) configured to apply the 1-D input vector to an ensemble stroke classification model (ESCM) (e.g., 140). The stroke detection device may, for example, include a processor (e.g., 205) operably coupled to the data store such that, when the processor executes the program of instructions, the processor causes operations to be performed to automatically and accurately predict whether a patient is experiencing a stroke. The operations may, for example, include receive a finite time window of a first predetermined duration of EEG data from a monitoring device operably coupled to the patient. The operations may, for example, include extract, by the feature extraction engine, at least four classes of features from the received EEG data. The operations may, for example, include aggregate the extracted features into the 1-D input vector. The operations may, for example, include apply the classification engine to the 1-D input vector such that the ESCM operates on the extracted features aggregated into the 1-D input vector. The operations may, for example, include generate, by the ESCM, a binary stroke prediction (e.g., 145). The operations may, for example, include generate and transmit a prediction signal to a user interface device such that an indication of the binary stroke prediction is provided to a user.

The ESCM may, for example, include a class-specific model set (e.g., 165, 170, 175, 180) for each of the classes of features, each set including multiple class-specific models for each of a corresponding group of architectures, each class-specific model configured to receive the 1-D input vector and operate on features of the corresponding class. The ESCM may, for example, include a general model set (e.g., 160) including multiple general models for each of a corresponding group of architectures, each general model configured to receive the 1-D input vector and operate on features of multiple of the classes. The binary stroke prediction may, for example, be generated based on a predetermined weighted aggregation of an output of each of the class-specific models and each of the general models. The class-specific models, the general models, and/or a meta model (e.g., generating a binary stroke prediction from the outputs of the class-specific and/or general models) may, for example, be configured such that a stroke prediction with an area under a receiver operating characteristic curve greater than 0.95 is determined in a finite time window of less than 10 minutes.

The monitoring device may, for example, include a headset configured to measure rolling windows of EEG data from the patient. The headset may, for example, include multiple electrodes configured to measure EEG data from the patient. A position of each of the electrodes may, for example, correlate with a corresponding brain region.

The stroke detection device may, for example, include a feedback module configured to receive the prediction signal and transmit an alert when the binary stroke prediction indicates that a stroke is detected.

The binary stroke prediction may, for example, include a prediction of a large vessel occlusion stroke. The SESCM may, for example, be trained using historic large vessel occlusion stroke data.

Each classification-specific model set may, for example, be created by training N predetermined models until a predetermined criterion is reached, and selecting from the N models a predetermined M number of models (e.g., where M<N) as the class-specific model set, wherein the M models having a closest result to a quality criterion. The quality criterion may, for example, be predetermined.

The at least four classes may, for example, include time series features, power spectrum density (e.g., PSD) features, quantitative EEG features, and brain symmetry features.

The corresponding group of architectures for each of the model sets may, for example, include gradient boosted machine, deep neural network, and distributed random forest.

The ESCM may, for example, be trained by generating a training input set by randomly selecting a finite time window of the first predetermined duration from a training data of a second predetermined duration longer than first predetermined duration.

The stroke detection device may, for example, include a user interface configured to receive a professional stroke prediction input indicating a human evaluation of a stroke prediction. The binary stroke prediction may, for example, be further generated based on the predetermined weighted aggregation including the professional stroke prediction input.

In an illustrative aspect, a computer program product (CPP) may, for example, include a program of instructions tangibly embodied on a non-transitory computer readable medium wherein, when the instructions are executed on a processor (e.g., 205), the processor causes stroke detection operations to be performed to automatically predict whether a patient is experiencing a stroke. The operations may, for example, include receive, from a monitoring device, a finite time window of a first predetermined duration of EEG data from the patient (e.g., 510). The operations may, for example, include extract at least four classes of features from the received EEG data (e.g., 515). The operations may, for example, include aggregating the extracted features into a 1-D input vector (e.g., 520). The operations may, for example, include apply an ensemble stroke classification model (e.g., ESCM) (e.g., 525) to the extracted features of the 1-D input vector. The operations may, for example, include generate, by the ESCM, a binary stroke prediction (e.g., 535) and output the binary stroke prediction to a human interface.

The ESCM may, for example, include a class-specific model set (e.g., 165, 170, 175, 180) for each of the classes of features. Each set may, for example, include multiple class-specific models for each of a corresponding group of architectures. Each class-specific model may, for example, be configured to receive the 1-D input vector and operate on features of the corresponding class. The ESCM may, for example, include a general model set (e.g., 160) including multiple general models for each of a corresponding group of architectures. Each general model may, for example, be configured to receive the 1-D input vector and operate on features of multiple of the classes. The binary stroke prediction may, for example, be generated based on a predetermined weighted aggregation of an output of each of the class-specific models and each of the general models.

The operations may, for example, include receive a professional input indicating a human evaluation of a stroke prediction. The operations may, for example, include generate the binary stroke prediction as a function of the professional inputs, outputs of the class-specific model sets, and outputs of the general model set based on a predetermined meta-learner model.

The binary stroke prediction may, for example, be a prediction of a large vessel occlusion stroke.

Each classification-specific model set may, for example, be created by training N predetermined models until a predetermined criterion is reached, and selecting from the N models a predetermined M number of models (e.g., where M<N) as the class-specific model set, wherein the M models having a closest result to a quality criterion. The quality criterion may, for example, be predetermined.

The at least four classes may, for example, include time series features, power spectrum density (e.g., PSD) features, PSD ratio features, and brain symmetry features.

The ESCM may, for example, be trained by generating a training input set by randomly selecting a finite time window of the first predetermined duration from a training data of a second predetermined duration longer than first predetermined duration.

In an illustrative aspect, a computer-implemented method may, for example, be performed by at least one processor (e.g., 205) to automatically and accurately predict whether a patient is experiencing a stroke in near real time. The method may, for example, include receive a finite time window of a first predetermined duration of EEG data from the patient (e.g., 510). The method may, for example, include extract at least four classes of features from the received EEG data (e.g., 515). The method may, for example, include aggregate the extracted features into a 1-D input vector (e.g., 520). The method may, for example, include apply the ensemble stroke classification model (e.g., ESCM) (e.g., 525) to the features of the 1-D input vector. The method may, for example, include generate, by the ESCM, a binary stroke prediction (e.g., 535).

The ESCM may, for example, include a class-specific model set (e.g., 165, 170, 175, 180) for each of the classes of features. Each set may, for example, include multiple class-specific models for each of a corresponding group of architectures. Each class-specific model may, for example, be configured to receive the 1-D input vector and operate on features of the corresponding class.

The ESCM may, for example, include a general model set (e.g., 160) including multiple general models for each of a corresponding group of architectures. Each general model may, for example, be configured to receive the 1-D input vector and operate on features of multiple of the classes.

The binary stroke prediction may, for example, be generated based on a predetermined weighted aggregation of an output of each of the class-specific models and each of the general models.

Each classification-specific model set may, for example, be created by training N predetermined models until a predetermined criterion is reached, and selecting from the N models a predetermined M number of models (e.g., where M<N) as the class-specific model set. The M models may, for example, be selected based on having a closest result to a quality criterion.

The at least four classes may, for example, include time series features, power spectrum density (e.g., PSD) features, PSD ratio features, and brain symmetry features.

The ESCM may, for example, be trained by generating a training input set by randomly selecting a finite time window of the first predetermined duration from a training data of a second predetermined duration longer than first predetermined duration.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A stroke detection device comprising:
a data store comprising a program of instructions, wherein the data store comprises:
a feature extraction engine configured to extract features from a rolling window of electroencephalogram (EEG) data to generate a 1-D input vector (135) of the extracted features; and,
a classification engine configured to apply the 1-D input vector to an ensemble stroke classification model (ESCM); and,
a processor operably coupled to the data store such that, when the processor executes the program of instructions, the processor causes operations to be performed to automatically and accurately predict whether a patient is experiencing a stroke, the operations comprising:
receive a finite time window of a first predetermined duration of EEG data from a monitoring device operably coupled to the patient;
extract, by the feature extraction engine, at least four classes of features from the received EEG data;
aggregate the extracted features into the 1-D input vector;
apply the classification engine to the 1-D input vector such that the ESCM operates on the extracted features aggregated into the 1-D input vector;
generate, by the ESCM, a binary stroke prediction; and,
generate and transmit a prediction signal to a user interface device such that an indication of the binary stroke prediction is provided to a user,
wherein:
the ESCM comprises:
a class-specific model set for each of the classes of features, each set comprising multiple class-specific models for each of a corresponding group of architectures, each class-specific model configured to receive the 1-D input vector and operate on features of the corresponding class; and,
a general model set including multiple general models for each of a corresponding group of architectures, each general model configured to receive the 1-D input vector and operate on features of multiple of the classes; and,
the binary stroke prediction is generated based on a predetermined weighted aggregation of an output of each of the class-specific models and each of the general models, such that a stroke prediction with an area under a receiver operating characteristic curve greater than 0.95 is determined in a finite time window of less than 10 minutes.

2. The stroke detection device of claim 1, further comprising the monitoring device, wherein the monitoring device comprises a headset configured to measure rolling windows of EEG data from the patient.

3. The stroke detection device of claim 2, wherein the headset further comprises a plurality of electrodes configured to measure EEG data from the patient, wherein a position of each of the plurality of electrodes correlates with a corresponding brain region.

4. The stroke detection device of claim 1, further comprising a feedback module configured to receive the prediction signal and transmit an alert when the binary stroke prediction indicates that a stroke is detected.

5. The stroke detection device of claim 1, wherein the binary stroke prediction comprises a prediction of a large vessel occlusion stroke, and wherein the ESCM is trained using historic large vessel occlusion stroke data.

6. The stroke detection device of claim 1, wherein each classification-specific model set is created by training N predetermined models until a predetermined criterion is reached, and selecting from the N models a predetermined M number of models (where M<N) as the class-specific model set, wherein the M models having a closest result to a quality criterion.

7. The stroke detection device of claim 1, wherein the at least four classes comprise time series features, power spectrum density (PSD) features, quantitative EEG features, and brain symmetry features.

8. The stroke detection device of claim 1, wherein the corresponding group of architectures for each of the model sets comprise gradient boosted machine, deep neural network, and distributed random forest.

9. The stroke detection device of claim 1, wherein the ESCM is trained by generating a training input set by randomly selecting the finite time window of the first predetermined duration from a training data of a second predetermined duration longer than the first predetermined duration.

10. The stroke detection device of claim 1, further comprising a user interface configured to receive a professional stroke prediction input indicating a human evaluation of a stroke prediction, wherein the binary stroke prediction is further generated based on the predetermined weighted aggregation including the professional stroke prediction input.

11. A computer program product (CPP) comprising a program of instructions tangibly embodied on a non-transitory computer readable medium wherein, when the instructions are executed on a processor, the processor causes stroke detection operations to be performed to automatically predict whether a patient is experiencing a stroke, the operations comprising:

receive, from a monitoring device, a finite time window of a first predetermined duration of electroencephalogram (EEG) data from the patient;

extract at least four classes of features from the received EEG data;

aggregate the extracted features into a 1-D input vector;

apply an ensemble stroke classification model (ESCM) to the extracted features of the 1-D input vector; and, generate, by the ESCM, a binary stroke prediction and output the binary stroke prediction to a human interface, wherein:

the ESCM comprises:

a class-specific model set for each of the classes of features, each set comprising multiple class-specific models for each of a corresponding group of architectures, each class-specific model configured to receive the 1-D input vector and operate on features of the corresponding class; and, a general model set including multiple general models for each of a corresponding group of architectures, each general model configured to receive the 1-D input vector and operate on features of multiple of the classes, and, the binary stroke prediction is generated based on a predetermined weighted aggregation of an output of each of the class-specific models and each of the general models.

12. The computer program product of claim 11, wherein the operations further comprise:

receive a professional input indicating a human evaluation of a stroke prediction; and, generate the binary stroke prediction as a function of the professional input, outputs of the class-specific model sets, and outputs of the general model set based on a predetermined meta-learner model.

13. The computer program product of claim 11, wherein the binary stroke prediction is a prediction of a large vessel occlusion stroke.

14. The computer program product of claim 11, wherein each classification-specific model set is created by training N predetermined models until a predetermined criterion is reached, and selecting from the N models a predetermined M number of models (where M<N) as the class-specific model set, wherein the M models having a closest result to a quality criterion.

15. The computer program product of claim 11, wherein the at least four classes comprise time series features, power spectrum density (PSD) features, PSD ratio features, and brain symmetry features.

16. The computer program product of claim 11, wherein the ESCM is trained by generating a training input set by randomly selecting the finite time window of the first predetermined duration from a training data of a second predetermined duration longer than the first predetermined duration.

17. A computer-implemented method performed by at least one processor (205) to automatically and accurately predict whether a patient is experiencing a stroke in near real time, the method comprising:

receive a finite time window of a first predetermined duration of electroencephalogram (EEG) data from the patient;

extract at least four classes of features from the received EEG data;

aggregate the extracted features into a 1-D input vector;

apply an ensemble stroke classification model (ESCM) to the features of the 1-D input vector; and, generate, by the ESCM, a binary stroke prediction, wherein:

the ESCM comprises:

a class-specific model set for each of the classes of features, each set comprising multiple class-specific models for each of a corresponding group of architectures, each class-specific model configured to receive the 1-D input vector and operate on features of the corresponding class; and, a general model set including multiple general models for each of a corresponding group of architectures, each general model configured to receive the 1-D input vector and operate on features of multiple of the classes, and, the binary stroke prediction is generated based on a predetermined weighted aggregation of an output of each of the class-specific models and each of the general models.

18. The computer-implemented method of claim 17, wherein each classification-specific model set is created by training N predetermined models until a predetermined criterion is reached, and selecting from the N models a predetermined M number of models (where M<N) as the class-specific model set, wherein the M models having a closest result to a quality criterion.

19. The computer-implemented method of claim 17, wherein the at least four classes comprise time series features, power spectrum density (PSD) features, PSD ratio features, and brain symmetry features.

20. The computer-implemented method of claim 17, wherein the ESCM is trained by generating a training input set by randomly selecting the finite time window of the first predetermined duration from a training data of a second predetermined duration longer than the first predetermined duration.

\* \* \* \* \*